(12) United States Patent
Blurton et al.

(10) Patent No.: US 7,442,701 B2
(45) Date of Patent: Oct. 28, 2008

(54) AMINO-HETEROCYCLES AS VR-1 ANTAGONISTS FOR TREATING PAIN

(75) Inventors: Peter Blurton, Hitchin (GB); Frank Burkamp, Bishops Stortford (GB); Stephen Robert Fletcher, Bishops Stortford (GB); Gregory John Hollingworth, Brentwood (GB); A. Brian Jones, Saffron Walden (GB); Edward Giles McIver, Sawbridgeworth (GB); Christopher Richard Moyes, Hertford (GB); Lauren Rogers, Braintree (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 605 days.

(21) Appl. No.: 10/534,584

(22) PCT Filed: Nov. 14, 2003

(86) PCT No.: PCT/GB03/04969

§ 371 (c)(1),
(2), (4) Date: May 11, 2005

(87) PCT Pub. No.: WO2004/046133

PCT Pub. Date: Jun. 3, 2004

(65) Prior Publication Data

US 2006/0040947 A1 Feb. 23, 2006

(30) Foreign Application Priority Data

Nov. 15, 2002 (GB) ................... 0226724.3

(51) Int. Cl.
*A61K 31/44* (2006.01)
*A61K 31/497* (2006.01)
*C07D 403/02* (2006.01)

(52) U.S. Cl. .............. 514/252.01; 514/255.05; 514/269; 514/275; 514/337; 544/238; 544/298; 544/333; 544/405; 546/256; 546/268.1

(58) Field of Classification Search .............. None
See application file for complete search history.

(56) References Cited

FOREIGN PATENT DOCUMENTS

| WO | WO 98/41508 A | 9/1998 |
| WO | WO 02/08221 A | 1/2002 |
| WO | WO 03/068749 A | 8/2003 |
| WO | WO 03/080578 A | 10/2003 |

OTHER PUBLICATIONS

Bold et al, Journal of Medicinal Chemistry, 2000, vol. 43, No. 16, p. 3200.*

* cited by examiner

Primary Examiner—Zinna N Davis
(74) Attorney, Agent, or Firm—Sylvia A. Ayler; William Krovatin

(57) ABSTRACT

The present invention provides a compound of formula (I): wherein V represents $NR^5$, O, S, SO or $S(O)_2$; W and X each independently represent CH or N; Y represents N, CH or C—$Ar_2$, with the proviso that at least one, but no more than two, of W, X and Y are N; Z represents CH or C—$Ar_2$, with the proviso that when Y is N or CH then Z is C—$Ar_2$, and with the further proviso that when Y is C—$Ar_2$ then Z is CH; $Ar_1$ represents a fused 9 or 10 membered heterobicyclic ring system containing one, two, three or four heteroatoms selected from nitrogen, oxygen and sulfur, wherein at least one of the rings in said ring system is aromatic; $Ar_2$ represents an aromatic ring selected from phenyl, pyridyl, pyrimidinyl and pyridazinyl which is optionally fused and substituted; $R^1$ represents halogen, hydroxy, oxo, $C_{1-6}$alkyl, $C_{2-6}$alkenyl, $C_{2-6}$alkynyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{3-5}$cycloalkyl$C_{1-4}$alkyl, cyano, nitro, $SR^6$, $SOR^6$, $SO_2R^6$, $COR^6$, $NR^3COR^6$, $CONR^3R^4$, $NR^3SO_2R^6$, $SO_2NR^3R^4$, —$(CH_2)_m$carboxy, esterified —$(CH_2)_m$carboxy or —$(CH_2)_m NR^3R^4$; $R^2$ represents hydrogen, halogen, hydroxy, $C_{1-6}$alkyl, halo$C_{1-6}$alkyl, $C_{3-7}$cycloalkyl, $C_{1-6}$alkoxy, halo$C_{1-6}$alkoxy, unsubstituted phenyl or phenyl substituted with one or two groups selected from halogen, $C_{1-6}$alkyl, halo$C_{1-6}$alkyl, $C_{3-7}$cycloalkyl, $C_{1-6}$alkoxy or halo$C_{1-6}$alkoxy; $R^3$ and $R^4$ are each independently hydrogen, $C_{1-6}$alkyl, $C_{2-6}$alkenyl, $C_{2-6}$alkynyl, $C_{3-7}$cycloalkyl or fluoro$C_{1-6}$alkyl; or $R^3$ and $R^4$ and the nitrogen atom to which they are attached together form a heteroaliphatic ring of 4 to 7 ring atoms, optionally substituted by one or two groups selected from hydroxy or $C_{1-4}$alkoxy, which ring may optionally contain as one of the said ring atoms an oxygen or a sulfur atom, S(O), $S(O)_2$, or $NR^5$; $R^5$ represents hydrogen, $C_{1-4}$alkyl, hydroxy$C_{1-4}$alkyl or $C_{1-4}$alkoxy$C_{1-4}$alkyl; $R^6$ represents hydrogen, $C_{1-6}$alkyl, fluoro$C_{1-6}$alkyl, $C_{3-7}$cycloalkyl, unsubstituted phenyl, or phenyl substituted with one or two groups selected from halogen, $C_{1-6}$alkyl, halo$C_{1-6}$alkyl, $C_{3-7}$cycloalkyl, $C_{1-6}$alkoxy or halo$C_{1-6}$alkoxy; m is either zero or an integer from 1 to 4; n is either zero or an integer from 1 to 3; or a pharmaceutically acceptable salt, N-oxide or a prodrug thereof; a pharmaceutical composition comprising it; its use in methods of treatment; use of it for the manufacture of a medicament for treating VR-1 related conditions such as those in which pain and/or inflammation predominate; and methods of treatment using it.

(I)

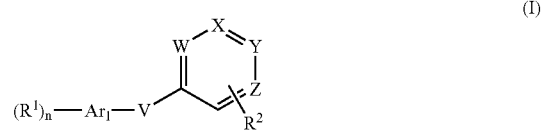

10 Claims, No Drawings

AMINO-HETEROCYCLES AS VR-1 ANTAGONISTS FOR TREATING PAIN

CROSS REFERENCE TO RELATED APPLICATIONS

This application claims the benefit of Great Britain Provisional Application No. 0226724.3 filed Nov. 15, 2002 and PCT/GB03/004969 filed Nov. 14, 2003.

The present invention is concerned with substituted amino-heterocycles and pharmaceutically acceptable salts and prodrugs thereof which are useful as therapeutic compounds, particularly in the treatment of pain and other conditions ameliorated by the modulation of the function of the vanilloid-1 receptor (VR1).

The pharmacologically active ingredient of chilli peppers has been recognised for some time to be the phenolic amide capsaicin. The application of capsaicin to mucous membranes or when injected intradermally, causes intense burning-like pain in humans. The beneficial effects of topical administration of capsaicin as an analgesic is also well established. However, understanding of the underlying molecular pharmacology mediating these responses to capsaicin has been a more recent development The receptor for capsaicin, termed the vanilloid VR1 receptor, was cloned by Caterina and colleagues at UCSF in 1997 (*Nature*, 398:816, 1997). VR1 receptors are cation channels that are found on sensory nerves that innervate the skin, viscera, peripheral tissues and spinal cord. Activation of VR1 elicits action potentials in sensory fibres that ultimately generate the sensation of pain. Importantly VR1 receptor is activated not only by capsaicin but also by acidic pH and by noxious heat stimuli. It is also sensitized by a number of inflammatory mediators and thus appears to be a polymodal integrator of painful stimuli.

The prototypical VR1 antagonist is capsazepine (Walpole et al., *J. Med. Chem.*, 37:1942, 1994)—VR1 $IC_{50}$ of 420 nM. A novel series of sub-micromolar antagonists has also been reported recently (Lee et al, *Bioorg. Med. Chem.*, 9:1713, 2001), but these reports provide no evidence for in vivo efficacy. A much higher affinity antagonist has been derived from the 'ultra-potent' agonist resiniferatoxin. Iodo-resiniferatoxin (Wahl et al., *Mol. Pharmacol.*, 59:9, 2001) is a nanomolar antagonist of VR1 but does not possess properties suitable for an oral pharmaceutical. This last is also true of the micromolar peptoid antagonists described by Garcia-Martinez (*Proc. Natl. Acad. Sci., USA*, 99:2374, 2002). Most recently International (PCT) patent publication No. WO 02/08221 has described a novel series of VR1 antagonists, which are stated to show efficacy in a number of animal models. We herein describe another novel series of VR1 modulators. These comprise predominantly VR1 antagonists but encompass VR1 partial antagonists and VR1 partial agonists. Such compounds have been shown to be efficacious in animal models of pain.

The present invention provides compounds of formula (I):

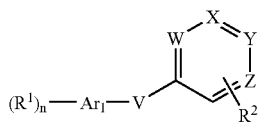

(I)

wherein
V represents $NR^5$, O, S, SO or $S(O)_2$;
W and X each independently represent CH or N;
Y represents N, CH or C—$Ar_2$, with the proviso that at least one, but no more than two, of W, X and Y are N;
Z represents CH or C—$Ar_2$, with the proviso that when Y is N or CH then Z is C—$Ar_2$, and with the further proviso that when Y is C—$Ar_2$ then Z is CH;
$Ar_1$ represents a fused 9 or 10 membered heterobicyclic ring system containing one, two, three or four heteroatoms selected from nitrogen, oxygen and sulfur, wherein at least one of the rings in said ring system is aromatic;
$Ar_2$ represents an aromatic ring selected from phenyl, pyridyl, pyridazinyl, pyrimidinyl and pyrazinyl; which aromatic ring is optionally fused to a phenyl ring, a five-membered heteroaromatic ring containing 1, 2, 3 or 4 heteroatoms selected from O, N and S at most 1 heteroatom being O or S, or a six-membered heteroaromatic ring containing 1, 2 or 3 N atoms; which aromatic ring is unsubstituted or substituted by one, two or three groups selected from halogen, hydroxy, $C_{1-6}$alkyl, $C_{2-6}$alkenyl, $C_{2-6}$alkynyl, phenyl$C_{1-2}$alkoxy, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-7}$cycloalkoxy, $C_{3-5}$cycloalkyl$C_{1-4}$alkyl, cyano, nitro, $SR^6$, $SOR^6$, $SO_2R^6$, $COR^6$, $NR^3COR^6$, $CONR^3R^4$, $NR^3SO_2R^6$, $SO_2NR^3R^4$, —$(CH_2)_m$carboxy, esterified —$(CH_2)_m$carboxy, —$(CH_2)_m NR^3R^4$, phenyl, naphthyl, a five-membered heteroaromatic ring containing 1, 2, 3 or 4 heteroatoms selected from O, N and S at most 1 heteroatom being O or S and a six-membered heteroaromatic ring containing 1, 2 or 3 N atoms; where two $C_1$ alkoxy groups are on adjacent atoms they may, together with the atoms to which they are attached, form a 5- or 6-membered partially saturated ring;
$R^1$ represents halogen, hydroxy, oxo, $C_{1-6}$allyl, $C_{2-6}$alkenyl, $C_{2-6}$alkynyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$Cycloalkyl, $C_{3-7}$cycloalkoxy, $C_{3-5}$cycloalkyl$C_{1-4}$alkyl, cyano, nitro, $SR^6$, $SOR^6$, $SO_2R^6$, $COR^6$, $NR^3COR^6$, $CONR^3R^4$, $NR^3SO_2R^6$, $SO_2NR^3R^4$, —$(CH_2)_m$carboxy, esterified —$(CH_2)_m$carboxy or —$(CH_2)_m NR^3R^4$;
$R^2$ represents hydrogen, halogen, hydroxy, $C_{1-6}$alkyl, halo$C_{1-6}$alkyl, $C_{3-7}$cycloalkyl $C_{1-6}$alkoxy, halo$C_{1-6}$alkoxy, unsubstituted phenyl or phenyl substituted with one or two groups selected from halogen, $C_{1-6}$alkyl, halo$C_{1-6}$alkyl, $C_{3-7}$cycloalkyl, $C_{1-6}$alkoxy or halo$C_{1-6}$alkoxy;
$R^3$ and $R^4$ are each independently hydrogen, $C_{1-4}$alkyl, $C_4$alkenyl, $C_{2-6}$alkynyl, $C_{3-7}$cycloalkyl or fluoro$C_{1-6}$alkyl; or $R^3$ and $R^4$ and the nitrogen atom to which they are attached together form a heteroaliphatic ring of 4 to 7 ring atoms, optionally substituted by one or two groups selected from hydroxy or $C_{1-4}$alkoxy, which ring may optionally contain as one of the said ring atoms an oxygen or a sulfur atom, S(O), $S(O)_2$, or $NR^5$;
$R^5$ represents hydrogen, $C_{1-4}$alkyl, hydroxy$C_{1-4}$alkyl or $C_{1-4}$alkoxy$C_{1-4}$alkyl;
$R^6$ represents hydrogen, $C_{1-6}$alkyl, fluoro$C_{1-6}$alkyl, $C_{3-7}$cycloalkyl, unsubstituted phenyl, or phenyl substituted with one or two groups selected from halogen, $C_{1-6}$alkyl, halo$C_{1-6}$alkyl, $C_{3-7}$cycloalkyl, $C_{1-6}$alkoxy or halo$C_{1-6}$alkoxy;
m is either zero or an integer from 1 to 4;
n is either zero or an integer from 1 to 3;
or a pharmaceutically acceptable salt, N-oxide or a prodrug thereof.

In one embodiment $Ar_2$ represents an aromatic ring selected from phenyl, pyridyl, pyridazinyl, pyrimidinyl and pyrazinyl, which aromatic ring is unsubstituted or substituted by one, two or three groups selected from halogen, hydroxy, $C_{1-6}$alkyl, $C_{2-6}$alkenyl, $C_{2-6}$alkynyl, halo$C_{1-6}$alkyl, hydroxy$C_{1-6}$alkyl, $C_{1-6}$alkoxy, halo$C_{1-6}$alkoxy, hydroxy$C_{1-6}$ alkoxy, $C_{3-7}$cycloalkyl, $C_{3-7}$cycloalkoxy, $C_{3-5}$cycloalkyl$C_{1-4}$ alkyl, cyano, nitro, $SR^6$, $SOR^6$, $SO_2R^6$, $COR^6$, $NR^3COR^6$, $CONR^3R^4$, $NR^3SO_2R^6$, $SO_2NR^3R^4$, —$(CH_2)_m$carboxy, esterified —$(CH_2)_m$carboxy and —$(CH_2)_m NR^3R^4$.

A preferred class of compound of formula (I) is that wherein $R^1$ is halogen, especially fluorine, $C_{1-4}$alkyl, especially methyl, or fluoro$C_{1-4}$alkyl, especially trifluoromethyl.

Preferably n is zero, one or two, and especially one or two.

A further preferred class of compound of formula (I) is that wherein $R^2$ is a hydrogen or a halogen atom, or a group selected from $C_{1-4}$alkyl, $C_{1-4}$alkoxy and phenyl substituted by $C_{1-4}$alkyl or fluoro$C_{1-4}$alkyl.

More particularly, $R^2$ preferably represents a hydrogen or chlorine atom or a group selected from methyl, methoxy and p-trifluoromethylphenyl. Most preferably, $R^2$ is a hydrogen atom or a methyl group.

It will be appreciated that the group $R^2$ is attached to any available carbon atom including those represented by W, X, Y and Z.

A further preferred class of compound of formula (I) is that wherein $R^3$ is a hydrogen atom or a $C_{1-4}$alkyl group, particularly a hydrogen atom or a methyl group, and most especially a hydrogen atom.

A yet further preferred class of compound of formula (I) is that wherein $R^4$ is a hydrogen atom or a $C_{1-4}$alkyl group, particularly a hydrogen atom or a methyl group, and most especially a hydrogen atom.

When present, $R^3$ is preferably a hydrogen atom or a $C_{1-4}$alkyl group, and $R^4$ is preferably a hydrogen atom or a $C_{1-4}$alkyl group, or the group $NR^3R^4$ represents a heteroaliphatic ring selected from azetidinyl, pyrrolidinyl, piperidinyl, morpholinyl, thiomorpholinyl, piperazinyl or a piperazinyl group substituted on the nitrogen atom by $C_{1-4}$alkyl optionally substituted by hydroxy or $C_{1-4}$alkoxy. More preferably, the group $NR^3R^4$ represents a group selected from —$NH_2$, —$NHCH_3$, —$N(CH_3)_2$, —$NHCH_2CH_3$, —$N(CH_3)CH_2CH_3$ and —$N(CH_2CH_3)_2$, and most especially, —$N(CH_3)_2$.

When present, $R^5$ is preferably hydrogen or $C_{1-4}$alkyl (e.g. methyl), and especially hydrogen.

Another preferred class of compound of formula (I) is that wherein V is NH or O and especially NH.

A further preferred class of compound of formula (I) is that wherein =W—X=Y— represents =N—CH=CH—, =N—N=CH—, =N—CH=N— or =N—N=C(Ar$_2$)—.

Particularly preferred are those compounds of formula (I) where W is N.

Also particularly preferred are those compounds of formula (I) where Y is N or CH.

A further preferred class of compound of formula (I) is that wherein Z is C—Ar$_2$.

Another preferred class of compound of formula (I) is that wherein Ar$_1$ represents a heterobicyclic ring system selected from isoquinoline, indazole, triazolopyridine (especially triazolo[1,5-a]pyridine), cinnoline, benzothiazole, imidazopyridine (especially imidazo[1,5-a]pyridine and imidazo[1,2-a]pyridine), quinolinone, tetrahydroisoquinoline, and dihydroquinolinone. Particularly preferred heterobicyclic ring systems are selected from isoquinoline, indazole, imidazo[1,5-a]pyridine, quinolin-2(1H)-one and 3,4dihydroquinolin-2(1H)-one. Most preferably, the group Ar$_1$ is attached to the remainder of the molecule through the carbon atom adjacent to one of the bridgehead atoms.

Thus Ar$_2$ may be phenyl or pyridyl which are optionally fused to a phenyl, imidazolyl or thienyl ring, and are unsubstituted or substituted by one to three groups independently selected from halogen, cyano, $C_{1-4}$alkyl, fluoro$C_{1-4}$alkyl, $C_{1-4}$alkoxy, fluoro$C_{1-4}$alkoxy, phenyl$C_{1-2}$alkoxy, piperidine optionally substituted by oxygen, $COR^6$ where $R^6$ is hydrogen or $C_{1-4}$alkyl, pyrazole, $C_{1-4}$alkylcarbonyl, carboxy, $C_{1-6}$alkylsulphonyl, nitro, phenyl, $C_{1-4}$alkylthio, hydroxy and —O—$CH_2$—O—.

Yet another preferred class of compound of formula (I) is that wherein Ar$_2$ represents unsubstituted phenyl or phenyl substituted by one or two substituents selected from halogen, cyano, $C_{1-4}$alkyl, fluoro$C_{1-4}$alkyl, $C_{1-4}$alkoxy and fluoro$C_{1-4}$ alkoxy. In particular, Ar$_2$ preferably represents a phenyl ring substituted by one substituent selected from fluorine, cyano, methyl, tert-butyl, trifluoromethyl, methoxy and trifluoromethoxy. Aptly, the substituent is attached at the 4-position of the phenyl ring.

Particular embodiments of Ar$_2$ include 4-trifluoromethylphenyl, pyrid-4-yl, 3-cyanophenyl, 4-methoxyphenyl, 4-tertbutylphenyl, 2-fluoro-4-trifluoromethylphenyl, 3-methylpyrid-2-yl and 4-fluorophenyl. Further embodiments of Ar$_2$ include 2,4-bis(trifluoromethyl)phenyl, 1-H-indol-5-yl, 1-benzothien-7-yl, 2-(4-oxopiperidin-1-ylmethyl)phenyl, 3-benzaldehyde, 4-ethylphenyl, 3-(imidazol-1-yl)phenyl, 3-fluorophenyl, 4-dimethylaminophenyl, quinolin-5-yl, 3,5-dichlorophenyl, 4-benzoxyphenyl, 3,5-bis(trifluoromethyl) phenyl, naphth-1-yl, 4-acetylphenyl, 4-cyanophenyl, 3-carboxyphenyl, 3-trifluoromethylphenyl, 3-methylphenyl, 2,4,6-trimethylphenyl, 2-fluoro-3-(pyrid-3-yl)phenyl, 4-methylsulphonylphenyl, naphth-2-yl, 4-ethoxyphenyl, 3-nitrophenyl, 4-chlorophenyl, biphen-4-yl, 1,3-benzodioxol-5-yl, 3-isopropylphenyl, 4-methylthiophenyl, 2,6-difluorophenyl, 4-hydroxyphenyl, 4-methoxyphenyl, phenyl and 4-trifluoromethoxyphenyl.

One favoured class of compound of the present invention is that of formula (Ia) and pharmaceutically acceptable salts, N-oxides and prodrugs thereof:

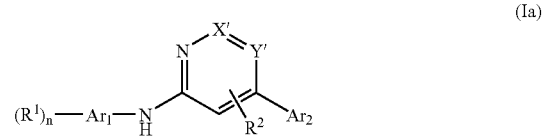

(Ia)

wherein —X'=Y'— represents —CH=CH—, —N=CH— or —CH=N—, and $R^1$, $R^2$, Ar$_1$, Ar$_2$ and n are as defined in formula (I).

Another favoured class of compound of the present invention is that of formula (Ib) and pharmaceutically acceptable salts, N-oxides and prodrugs thereof:

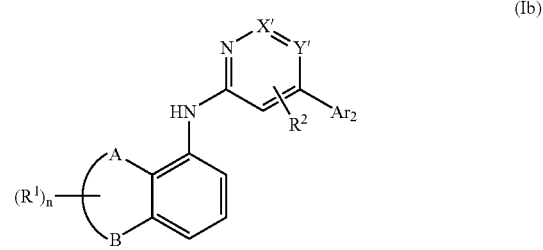

(Ib)

wherein —X'=Y'— represents —CH=CH—, —N=CH— or —CH=N—, -A-B— is selected from the group consisting of:
(a) —CH=CH—N=CH—,
(b) —CH=CH—CH=N—,
(c) —CH=CH—N=N—,
(d) —CH=N—N=CH—,
(e) —CH=N—CH=N—,
(f) —N=CH—CH=N—,
(g) —CH=CH—NH—,
(h) —CH=CH—O—,
(i) —CH=CH—S—,
(j) —N=CH—NH—,
(k) —CH=N—NH—
(l) —O—CH=N—,
(m) —CH=N—O—,
(n) —S—CH=N—,
(o) —CH=N—S—,
(p) —N=N—NH—,
(q) —CH$_2$—CH$_2$—CH=N—,
(r) —CH$_2$—CH$_2$—CH$_2$—NH—,
(s) —CH$_2$—CH$_2$—N=CH—,
(t) —CH$_2$—CH$_2$—NH—CH$_2$—,
(u) —CH$_2$—NH—C(O)—NH—,
(v) —CH$_2$—O—C(O)—NH—,
(w) —CH$_2$—NH—S(O)—NH—,
(x) —CH$_2$—NH—SO$_2$—NH—,
(y) —CH$_2$—CH$_2$—C(O)—NH—, and
(z) —CH=CH—C(O)—NH—;

and R$^1$ (which may be on either or both of the rings of the heterobicyclic ring system), R$^2$, Ar$_2$ and n are as defined in formula (I).

Another favoured class of compound of the present invention is that of formulae (Ic) and (Id) and pharmaceutically acceptable salts, N-oxides and prodrugs thereof:

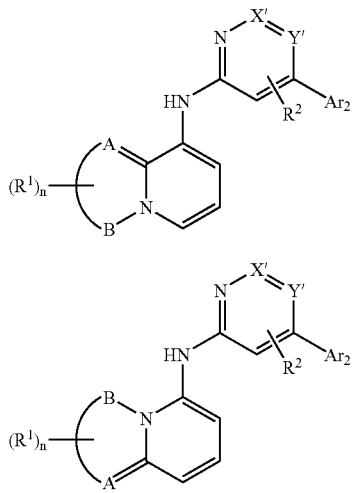

wherein —X'=Y'— represents —CH=CH—, —N=CH— or —CH=N—, -A-B— is selected from the group consisting of:
(a) =CH—CH=N—,
(b) =CH—N=CH—,
(c) =N—CH=CH—, and
(d) =CH—CH=CH—;

and R$^1$ (which may be on either or both of the rings of the heterobicyclic ring system), R$^2$, Ar$_2$ and n are as defined in formula (I).

A further favoured class of compound of the present invention is that of formulae (Ie) and pharmaceutically acceptable salts, N-oxides and prodrugs thereof:

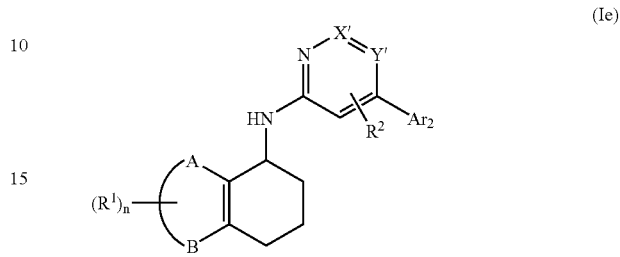

wherein —X'=Y'— represents —CH=CH—, —N=CH— or —CH=N—, -A-B— is selected from the group consisting of:
(a) —CH=CH—CH=N—,
(b) —CH=CH—N=CH—,
(c) —CH=N—CH=CH—,
(d) —N=CH—CH=CH—,
(e) —CH=CH—NH—,
(f) —CH=N—NH—,
(g) —N=CH—NH—, and
(h) —CH=CH—O—;

and R$^1$ (which may be on either or both of the rings of the heterobicyclic ring system), R$^2$, Ar$_2$ and n are as defined in formula (I).

When any variable occurs more than one time in any of formulae (I), (Ia), (Ib), (Ic), (Id) and (Ie) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the term "hydroxyC$_{1-6}$alkyl" means a C$_{1-6}$alkyl group in which one or more (in particular 1 to 3, and especially 1) hydrogen atoms have been replaced by hydroxy groups. Particularly preferred are hydroxyC$_{1-3}$alkyl groups, for example, CH$_2$OH, CH$_2$CH$_2$OH, CH(CH$_3$)OH or C(CH$_3$)$_2$OH, and most especially CH$_2$OH.

As used herein, the terms "haloC$_{1-6}$alkyl" and "haloC$_{1-6}$alkoxy" means a C$_{1-6}$alkyl or C$_{1-6}$alkoxy group in which one or more (in particular, 1 to 3) hydrogen atoms have been replaced by halogen atoms, especially fluorine or chlorine atoms. Preferred are fluoroC$_{1-6}$alkyl and fluoroC$_{1-6}$alkoxy groups, in particular, fluoroC$_{1-3}$alkyl and fluoroC$_{1-3}$alkoxy groups, for example, CF$_3$, CH$_2$CH$_2$F, CH$_2$CHF$_2$, CH$_2$CF$_3$, OCF$_3$, OCH$_2$CH$_2$F, OCH$_2$CHF$_2$ or OCH$_2$CF$_3$, and most especially CF$_3$, OCF$_3$ and OCH$_2$CF$_3$.

The cycloalkyl groups referred to herein may represent, for example, cyclopropyl, cyclobutyl, cyclopentyl or cyclohexyl. Suitable C$_{3-7}$cycloalkylC$_{1-4}$alkyl groups include, for example, cyclopropylmethyl and cyclohexylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is acetylene or propargyl.

When used herein, the term "halogen" means fluorine, chlorine, bromine and iodine. The most apt halogens are fluorine and chlorine of which fluorine is preferred, unless otherwise stated.

When used herein, the term "carboxy" as a group or part of a group denotes $CO_2H$.

When used herein, the term "esterified carboxy" denotes a $C_{1-6}$alkoxy or a halo$C_{1-6}$alkoxy radical attached via the oxygen atom thereof to a carbonyl (C=O) radical thus forming a $C_{1-6}$alkoxycarbonyl or halo$C_{1-6}$alkoxycarbonyl radical. Suitable examples of such esterified carboxy groups include, for example, methoxycarbonyl, ethoxycarbonyl, propoxycarbonyl, isopropoxycarbonyl and tert-butoxycarbonyl.

As used herein, the term "fused 9 or 10 membered heterobicyclic ring system" means a 5,6-, 6,5- or 6,6-fused ring system wherein one or both rings contain ring heteroatoms. The ring system is preferably aromatic or partially saturated, thus the ring system preferably comprises an aromatic 6-membered ring fused to a 5- or 6-membered ring which may be unsaturated, partially saturated or saturated. When the ring system contains more than one ring heteroatom at least one such heteroatom is-nitrogen. It will be appreciated that where one of the ring heteroatoms is a nitrogen atom, such heteroatom may be at the bridgehead position of the fused ring system. It will also be appreciated that where one of the ring heteroatoms in a saturated ring is sulfur, such heteroatom may be oxidized to a S(O) or $S(O)_2$ moiety. Likewise, any carbon atom in a saturated ring may be oxidized to a C=O moiety.

Suitable examples of a "fused 9 or 10 membered heterobicyclic ring system" include isoquinolinyl, quinolinyl, cinnolinyl, phthalazinyl, quinazolinyl, quinoxalinyl, naphthyridinyl, indolyl, isoindolyl, benzofuranyl, benzothiophenyl, benzimidazolyl, indazolyl, benzoxazolyl, benzisoxazolyl, benzothiazolyl, benzisothiazolyl, benzotriazole, pyridopyridazinyl, pyridopyrimidinyl, pyridopyrazinyl, pyrrolopyridinyl, furopyridinyl, thienopyridinyl, pyrrolopyridazinyl, fuiropyridazinyl, thienopyridazinyl, pyrrolopyrimidinyl, fuiropyrimidinyl, thienopyrirnidinyl, pyrrolopyrazinyl, fuiropyrazinyl, thienopyrazinyl, imidazopyridinyl, pyrazolopyridinyl, oxazolopyridinyl, isoxazolopyridinyl, thiazolopyridinyl, isothiazolopyridinyl, imidazopyridazinyl, pyrazolopyridazinyl, oxazolopyridazinyl, isoxazolopyridazinyl, thiazolopyridazinyl, isothiazolopyridazinyl, imidazopyrimidinyl, pyrazolopyrimidinyl, oxazolopyrimidinyl, isoxazolopyrimidinyl, thiazolopyrimidinyl, isothiazolopyrimidinyl, imidazopyrazinyl, pyrazolopyrazinyl, oxazolopyrazinyl, isoxazolopyrazinyl, thiazolopyrazinyl, isothiazolopyrazinyl, triazolopyridinyl, benzotriazolyl, quinolinonyl, isoquinolinonyl, dihydroquinolinonyl, dihydroisoquinolinonyl, tetrahydroquinolinyl, tetrahydroisoquinolinyl, dihydroquinazolinonyl, dihydrobenzoxainonyl, dihydrobenzothiadiazine oxide and dihydrobenzothiadiazine dioxide.

Thus the present invention provides a compound which is:
N-(4-phenylpyridin-2-yl)isoquinolin-5-amine;
N-{4-[4-trifluoromethoxyphenyl]pyridin-2-yl}isoquinolin-5-amine;
N-{4-[3-trifluoromethylphenyl]pyridin-2-yl}isoquinolin-5-amine;
N-{4-[4-trifluoromethylphenyl]pyridin-2-yl}isoquinolin-5-amine;
N-{5-[4-trifluoromethylphenyl]pyridin-2-yl}isoquinolin-5-amine;
5-({4-[4-trifluoromethylphenyl]pyridin-2-yl}oxy)isoquinoline;
N-{6-methyl-4-[4-trifluoromethylphenyl]pyridin-2-yl}isoquinolin-5-amine;
N-{6-methoxy-4-[4-trifluoromethylphenyl]pyridin-2-yl}isoquinolin-5-amine;
N-{6-chloroA[4-trifluoromethyl)phenyl]pyridin-2-yl}isoquinolin-5-amine;
N-{6-chloro-4-(pyridin-4-yl)pyridin-2-yl}isoquinolin-5-amine;
3-methyl-N-{4-[4-trifluoromethylphenyl]pyridin-2-yl}isoquinolin-5-amine;
1-methyl-N-{-[4-trifluoromethylphenyl]pyridin-2-yl}isoquinolin-5-amine;
6,8-difluoro-3-methyl-N-{4-[4-trifluoromethylphenyl]pyridin-2-yl}isoquinolin-5-amine;
3-methyl-7-trifluoromethyl-N-{4-[4-trifluoromethylphenyl]pyridin-2-yl}isoquinolin-5-amine;
8-fluoro-3-methyl-N-{4-[4-triuoromethylphenyl]pyridin-2-yl}isoquinolin-5-amine;
6-fluoro-3-methyl-N-{4-[4-trifluoromethylphenyl]pyridin-2-yl}quinolin-5-amine;
N-{4-[4-trifluoromethylphenyl]pyridin-2-yl}quinolin-5-amine;
3-methyl-N-{4-[4-trifluoromethylphenyl]pyridin-2-yl}cinnolin-5-amine;
1-methyl-5-({4-[4-trifluoromethylphenyl]pyridin-2-yl}amino)quinolin-2(1H)-one;
1-methyl-5-({4-[4-trifluoromethylphenyl]pyridin-2-yl}amino)-3,4-dihydroquinolin-2(1H)-one;
1-methyl-N-{4-[4-trifluoromethylphenyl]pyridin-2-yl}-1H-indazol-4-amine;
N-{4-[4-trifluoromethylphenyl]pyridin-2-yl}-1H-indazol-4-amine;
6-fluoro-1-methyl-N-{4-[4-trifluoromethylphenyl]pyridin-2-yl}-1H-indazol-4-amine;
1-methyl-6-trifluoromethyl-N-{4-[4-trifluoromethylphenyl]pyridin-2-yl}-1H-indazol-4-amine;
N-{5-[4-trfluoromethylphenyl]pyridazin-3-yl}isoquinolin-5-amine;
N-(5-[3-cyanophenyl]pyridazin-3-yl)isoquinolin-5-amine;
N-[5-(4-methoxyphenyl)pyridazin-3-yl)isoquinolin-5-amine;
N-[5-(4-tert-butylphenyl)pyridazin-3-yl]isoquinolin-5-amine;
N-{5-[2-fluoro trifluoromethylphenyl]pyridazin-3-yl}isoquinolin-5-amine;
N-{6-chloro-5-[4-trifluoromethylphenyl]pyridazin-3-yl}isoquinolin-5-amine;
N-[5-(3-methylpyridin-2-yl)pyridazin-3-yl]isoquinolin-5-amine;
N-{4,5-bis[4-trifluoromethylphenyl]pyridazin-3-yl}isoquinolin-5-amine;
3-methyl-N-{5-[4-trifluoromethylphenyl]pyridazin-3-yl}isoquinolin-5-amine;
1-methyl-N-{5-[4-trifluoromethylphenyl]pyridazin-3-yl}isoquinolin-5-amine;
N-{5-[4-trifluoromethylphenyl]pyridazin-3-yl}-5,6,7,8-tetrahydroisoquinolin-5-amine;
6,8-difluoro-3-methyl-N-{5-[4-trifluoromethylphenyl]pyridazin-3-yl}isoquinolin-5-amine;
3-methyl-7-trifluoromethyl-N-{5-[4-trifluoromethylphenyl]pyridazin-3-yl}isoquinolin-5-amine;
8-fluoro-3-methyl-N-{5-[4-trifluoromethylphenyl]pyridazin-3-yl}isoquinolin-5-amine;
6-fluoro-3-methyl-N-{5-[4-trifluoromethylphenyl]pyridazin-3-yl}isoquinolin-5-amine;

3-methyl-N-{5-[4-trifluoromethylphenyl]pyridazin-3-yl}cinnolin-5-amine;
1-methyl-5-({5-[4-trifluoromethylphenyl]pyridazin-3-yl}amino)quinolin-2(1H)-one;
1-methyl-N-{5-[4-trifluoromethylphenyl]pyridazin-3-yl}-1H-indazol-4-amine;
2-methyl-N-{5-[4-trifluoromethylphenyl]pyridazin-3-yl}-2H-indazol-4-amine;
N-{5-[4-trifluoromethylphenyl]pyridazin-3-yl}-1H-indazol-4-amine;
6-fluoro-1-methyl-N-{5-[4-trifluoromethylphenyl]pyridazin-3-yl}-1H-indazol-4-amine;
1-methyl-6-trifluoromethyl-N-{5-[4-trifluoromethylphenyl]pyridazin-3-yl}-1H-indazol-4-amine;
N-{5-[4-trifluoromethylphenyl]pyridazin-0.3-yl}imidazo[1,5-a]pyridin-8-amine;
N-{5-[4-trifluoromethylphenyl]pyridazin-3-yl}imidazo[1,2-a]pyridin-5-amine;
N-{5-[4-trifluoromethylphenyl]pyridazin-3-yl}[1,2,3]triazolo[1,5-a]pyridin-4-amine;
2-methyl-N-{5-[4-trifluoromethylphenyl]pyridazin-3-yl}-1,3-benzothiazol-6-amine;
N-{6-(4-fluorophenyl)pyridazin-4-yl}isoquinolin-5-amine;
N-{6-[4-trifluoromethylphenyl]pyrimidinyl}isoquinolin-5-amine;
3-methyl-N-{6-[4-trifluoromethylphenyl]pyrimidin-4-yl}isoquinolin-5-amine;
1-methyl-N-{6-[4-trifluoromethylphenyl]pyrimidin-4-yl}isoquinolin-5-amine;
N-{6-[4-trifluoromethylphenyl]pyrimidin-4-yl}-5,6,7,8-tetrahydroisoquinolin-5-amine;
6,8-difluoro-3-methyl-N-{6-[4-trifluoromethylphenyl]pyrimidin-4-yl}isoquinolin-5-amine;
3-methyl-7-trifluoromethyl-N-{6-[4-trifluoromethylphenyl]pyrimidin-4-yl}isoquinolin-5-amine;
8-fluoro-3-methyl-N-{6-[4-trifluoromethylphenyl]pyrimidin-4-yl}isoquinolin-5-amine;
6-fluoro-3-methyl-N-{6-[4-trifluoromethylphenyl]pyrimidinyl}isoquinolin-5-amine;
3-methyl-N-{2-methyl-6-[4-trifluoromethylphenyl]pyrimidin-4-yl}isoquinolin-5-amine;
3-methyl-N-{6-[4-trifluoromethylphenyl]pyrimidin-4-yl}cinnolin-5-amine;
1-methyl-N-{6-[4-trifluoromethylphenyl]pyrimidin-4-yl}-1H-indazol-4-amine;
N-{6-[4-trifluoromethylphenyl]pyrimidin-4-yl}-1H-indazol-4-amine;
6-fluoro-1-methyl-N-{6-[4-trifluoromethylphenyl]pyrimidin-4-yl}-1H-indazol-4-amine;
1-methyl-6-trifluoromethyl-N-{6-[4-trifluoromethylphenyl]pyrimidin-4-yl)-1H-indazol-4-amine;
N-{6-[4-trifluoromethylphenyl]pyrimidin-4-yl}[1,2,3]triazolo[1,5-a]pyridin amine;
1,3-dimethyl-5-((6-[4-trifluoromethylphenyl]pyrimidin-4-yl}amino)quinolin-2(1H)-one;
1,3-dimethyl-5-({5-[4-trifluoromethylphenyl]pyridazin-3-yl}amino)quinolin-2(1H)-one;
1,3-dimethyl-5-({4-[4-trifluoromethylphenyl]pyridin-2-yl}amino)quinolin-2(1H)-one;
N-{5-methoxy-6-[4-trifluoromethylphenyl]pyrimidin-4-yl}isoquinolin-5-amine;
N-{5-methyl-6-[4-trifluoromethylphenyl]pyrimidin-4-yl}isoquinolin-5-amine;
N-{6-[2,4-bis(trifluoromethyl)phenyl]pyrimidin-4-yl}isoquinolin-5-amine;
N-{6-(1H-indol-5-yl)pyrimidin-4-yl}isoquinolin-5-amine;
N-{6-(1-benzothien-7-yl)pyrimidin-4-yl}isoquinolin-5-amine;
1-{2-[6-(isoquinolin-5-ylamino)pyrimidin-4-yl]benzyl}piperidin-4-one;
3-[6-(isoquinolin-5-ylamino)pyrimidin-4-yl]benzaldehyde;
N-{6-(4-ethylphenyl)pyrimidin-4-yl}isoquinolin-5-amine;
N-{6-[3-(1H-pyrazol-1-yl)phenyl]pyrimidin-4-yl}isoquinolin-5-amine;
N-{6-(3-fluorophenyl)pyrimidin-4-yl}isoquinolin-5-amine;
N-{6-[4-dimethylaminophenyl]pyrimidin-4-yl}isoquinolin-5-amine;
N-(6-quinolin-8-ylpyrimidin-4-yl)isoquinolin-5-amine;
N-{6-(3,5-dichlorophenyl)pyrimidin-4-yl}isoquinolin-5-amine;
N-{6-[4-benzyloxyphenyl]pyrimidin-4-yl}isoquinolin-5-amine;
N-{6-[4-trifluoromethoxyphenyl]pyrimidin-4-yl}isoquinolin-5-amine;
N-{6-[3,5-bis(trifluoromethyl)phenyl]pyrimidin-4-yl}isoquinolin-5-amine;
N-{6-(1-naphthyl)pyrimidinyl}isoquinolin-5-amine;
N-{6-(4-tert-butylphenyl)pyrimidin-4-yl}isoquinolin-5-amine
1-{4-[6-(isoquinolin-5-ylamino)pyrimidin-4-yl]phenyl}ethanone;
4-[6-(isoquinolin-5-ylamino)pyrimidin-4-yl]benzonitrile;
3-[6-(isoquinolin-5-ylamino)pyrimidin-4-yl]benzoic acid;
N-{6-[3-trifluoromethylphenyl]pyrimidin-4-yl}isoquinolin-5-amine;
N-[6-(3-methylphenyl)pyrimidinyl]isoquinolin-5-amine;
N-(6-tesitylpyrimidinyl)isoquinolin-5-amine;
N-{6-(2-fluoro-3-pyridin-3-ylphenyl)pyrimidin-4-yl}isoquinolin-5-amine;
N-{6-[4-methylsulfonylphenyl]pyrimidinfyl}isoquinolin-5-amine;
N-{6-(2-naphthyl)pyrimidin-4-yl}isoquinolin-5-amine;
N-{6-(4-ethoxyphenyl)pyrimidin-4-yl}isoquinolin-5-amine;
N-{6-(3-nitrophenyl)pyrimidin-4-yl}isoquinolin-5-amine;
N-{6-(4-chlorophenyl)pyrimidin-4-yl}isoquinolin-5-amine;
N-(6-biphenyl-4-ylpyrimidin-4-yl)isoquinolin-5-amine;
N-{6-(1,3-benzodioxol-5-yl)pyrimidin-4-yl}isoquinolin-5-amine;
N-{6-(3-isopropylphenyl)pyrimidinyl}isoquinolin-5-amine;
N-{6-[4-methylthiophenyl]pyrimidin-4-yl}isoquinolin-5-amine;
N-{6-(2,5-difluorophenyl)pyrimidin-4-yl}isoquinolin-5-amine;
4-[6-(isoquinolin-5-ylamino)pyrimidin-4-yl]phenol;
N-{6-(4-methoxyphenyl)pyrimidinA-yl}isoquinolin-5-amine;
N-(6-phenylpyrimidin-4-yl)isoquinolin-5-amine;
6-fluoro-3-methyl-N-{2-methyl-6-[4-trifluoromethylphenyl]pyrimidin-4-yl}isoquinolin-5-amine;
N-{6-(4-chlorophenyl)pyrimidin-4-yl}-6-fluoro-3-methyl-isoquinolin-5-amine; or
6-fluoro-3-methyl-N-{6-[4-trifluoromethoxyphenyl]pyrimidin-4-yl}isoquinolin-5-amine;

or a pharmaceutically acceptable salt thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the compound of formula (I) with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention also includes within its scope N-oxides of the compounds of formula (I) above. In general, such N-oxides may be formed on any available nitrogen atom. The N-oxides may be formed by conventional means, such as reacting the compound of formula (I) with oxone in the presence of wet alumina.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention may have one or more asymmetric centres, and may accordingly exist both as enantiomers and as diastereoisomers. It is to be understood that all such isomers and mixtures thereof are encompassed within the scope of the present invention. Furthermore, the compounds of formula (I) may also exist in tautomeric forms and the invention includes within its scope both mixtures and separate individual tautomers.

It will be appreciated that the preferred definitions of the various substituents recited herein may be taken alone or in combination and, unless otherwise stated, apply to the generic formula for compounds of the present invention as well as to the preferred classes of compound represented by formulae (Ia), (Ib), (Ic), (Id) and (Ie).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, sterile parenteral solutions or suspensions, metered aerosol or liquid sprays, drops, ampoules, auto-injector devices, suppositories, creams or gels; for oral, parenteral, intrathecal, intranasal, sublingual, rectal or topical administration, or for administration by inhalation or insufflation. Oral compositions such as tablets, pills, capsules or wafers are particularly preferred. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation composition is then subdivided into unit dosage forms of the type described above containing from 0.1 to about 500 mg of the active ingredient of the present invention. Favoured unit dosage forms contain from 1 to 500 mg, for example 1, 5, 10, 25, 50, 100, 300 or 500 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of painful conditions such as those listed below, a suitable dosage level is about 1.0 mg to 15 g per day, preferably about 5.0 mg to 5 g per day, and especially about 20 mg to 2 g day. The compounds may be administered on a regimen of 1 to 4 times per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The invention further provides a compound of formula (I) as defined above, or a pharmaceutically acceptable salt thereof, for use in treatment of the human or animal body.

Preferably, said treatment is for a condition which is susceptible to treatment by modulation (preferably antagonism) of VR1 receptors.

The compounds of the present invention will be of use in the prevention or treatment of diseases and conditions in which pain and/or inflammation predominates, including chronic and acute pain conditions. Such conditions include rheumatoid arthritis; osteoarthritis; post-surgical pain; musculo-skeletal pain, particularly after trauma; spinal pain; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, for example, odontalgia, abdominal pain, gynaecological pain, for example, dysmenorrhoea, pain associated with cystitis and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; itching conditions including pruritis, itch due to hemodialysis, and contact dermatitis; pain (as well as broncho-constriction and inflammation) due to exposure (e.g. via ingestion, inhalation, or eye contact) of mucous membranes to capsaicin and related irritants such as tear gas, hot peppers or pepper spray; neuropathic pain conditions such as diabetic neuropathy, chemotherapy-induced neuropathy and post-herpetic neuralgia; "non-painfil" neuropathies; complex regional pain syndromes; pain associated with carcinoma, often referred to as cancer pain; central nervous system pain, such as pain due to spinal cord or brain stem damage, low back pain, sciatica and ankylosing spondylitis; gout; scar pain; irritable bowel syndrome; inflammatory bowel disease; urinary incontinence including bladder detrusor hyper-reflexia and bladder hyper-sensitivity; respiratory diseases including chronic obstructive pulmonary disease (COPD), chronic bronchitis, cystic fibrosis, asthma and rhinitis, including allergic rhinitis such as seasonal and perennial rhinitis, and non-allergic rhinitis; autoimmune diseases; and immunodeficiency disorders.

Thus, according to a further aspect, the present invention provides a compound of formula (I) for use in the manufacture of a medicament for the treatment or prevention of physiological disorders that may be ameliorated by modulating VR1 activity.

The present invention also provides a method for the treatment or prevention of physiological disorders that may be ameliorated by modulating VR1 activity, which method comprises administration to a patient in need thereof of an effective amount of a compound of formula (I) or a composition comprising a compound of formula (I).

According to a further or alternative aspect, the present invention provides a compound of formula (I) for use in the manufacture of a medicament for the treatment or prevention of a disease or condition in which pain and/or inflammation predominates.

The present invention also provides a method for the treatment or prevention of a disease or condition in which pain and/or inflammation predominates, which method comprises administration to a patient in need thereof of an effective amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination. Thus, for example, for the treatment or prevention of pain and/or inflammation, a compound of the present invention may be used in conjunction with other analgesics, such as acetaminophen (paracetamol), aspirin and other NSAIDs, including selective cyclooxygenase-2 (COX-2) inhibitors, as well as opioid analgesics, especially morphine, NR2B antagonists, bradykinin antagonists, anti-migraine agents, anticonvulsants such as oxcarbazepine and carbamazepine, antidepressants (such as TCAs, SSRIs, SNRIs, substance P antagonists, etc.), spinal blocks, gabapentin, pregabalin and asthma treatments (such as $\theta_2$-adrenergic receptor agonists or leukotriene $D_4$ antagonists (e.g. montelukast).

Specific anti-inflammatory agents include diclofenac, ibuprofen, indomethacin, nabumetone, ketoprofen, naproxen, piroxicam and sulindac, etodolac, meloxicam, rofecoxib, celecoxib, etoricoxib, parecoxib, valdecoxib and tilicoxib. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Suitable anti-migraine agents of use in conjunction with a compound of the present invention include CGRP-antagonists, ergotamines or 5-$HT_1$ agonists, especially sumatriptan, naratriptan, zolmatriptan or rizatriptan.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of a disease or condition in which pain and/or inflammation predominates.

According to a general process (A), compounds of formula (I), in which V is $NR^5$, may be prepared by the reaction of an amine of formula (II) with a compound of formula (III):

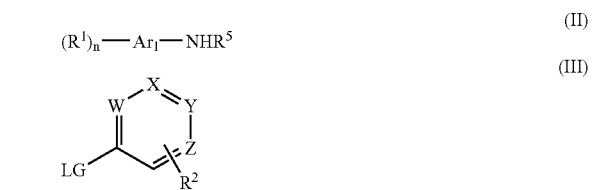

wherein LG is a suitable leaving group such as an alkyl- or arylsulfonyloxy group (e.g. mesylate or tosylate) or a halogen atom (e.g. bromine, chlorine or iodine). Preferably the leaving group is chlorine, bromine, iodine or triflate, and especially chlorine.

The reaction is conveniently effected under conditions suitable for a Buchwald-Hartwig Cross-Coupling Reaction (for review, see for instance J. F. Hartwig, *Angew. Chem. Int. Ed.*, 1998, 37, 2046-2067). The reaction is effected in the presence of complex of a palladium catalyst with a chelating phosphine ligand.

Suitable palladium catalysts include: tris(dibenzylideneacetone)dipalladium(0) [Pd$_2$(dba)$_3$], Pd(dba)$_2$, and 2'-(dimethylamino)-2-biphenylyl palladium (II) chloride.

Suitable chelating phosphine ligands include: 2-(dicyclohexylphosphino)biphenyl, 2,2'-bis(diphenylphosphanyl)-1,1'-binaphthyl [BINAP], 2,2'-bis(di-ptolylphosphanyl)-1,1'-binaphthyl [Tol-BINAP], propane-1,3-diylbis(diphenylphosphane) [DPPP] and dinorbornylphosphine. 4,5-Bis(diphenylphosphino)-9,9-dimethylxanthene may also be used.

The reaction is also conveniently effected in the presence of a base such as potassium carbonate or, more typically, sodium tert-butoxide. Caesium carbonate may also be used.

The reaction is conveniently effected at a temperature between 80° C. and 140° C., conveniently at about 100° C. Suitable solvents include, for example, p-xylene, toluene or dioxane.

It will be appreciated that whilst the leaving group in general process (A) is depicted on the compound of formula (III), it may be desirable in certain circumstances to have the leaving group on the Ar$_1$ intermediate, and for the central heteroaromatic ring to be substituted by the NHR$^5$ moiety.

If the heteroaromatic compound of formula (III) is sufficiently electrophilic and the amine of formula (II) sufficiently nucleophilic, formation of the N-aryl bond may be accomplished using a nucleophilic substitution (SN$_{Ar}$) reaction. This is the case for example where the amine is benzylic and the heteroaromatic compound is electron poor.

Thus, according to a further general process (B), compounds of formula (I) in which Ar$_1$ comprises a saturated or partially saturated 6-membered ring to which is fused an aromatic 5- or 6-membered ring, and V is NR$^5$, may be prepared by the reaction of a compound of formula (III) with an amine of formula (V):

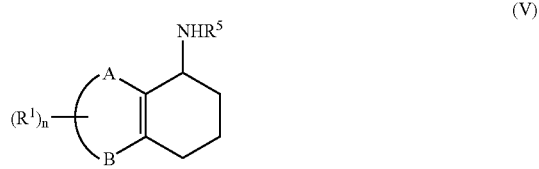

(V)

wherein -A-B— represents a 3- or 4-atom chain that completes the aromatic 5- or 6-membered ring, said chain containing between 1 and 4 (preferably 1 or 2) heteroatoms selected from N, O and S. Aptly, -A-B— represents:
 (a) —CH=CH—CH=N—,
 (b) —CH=CH—N=CH—,
 (c) —CH=N—CH=CH—,
 (d) —N=CH—CH=CH—,
 (e) —CH=CH—NH—,
 (f) —CH=N—NH—,
 (g) —N=CH—NH—, and
 (h) —CH=CHO—;

and R$^1$, where present, may be on either or both of the rings of the heterobicyclic ring system.

The reaction may be effected in the presence of a base, if desired, and a suitable solvent such as dimethylacetamide, and is generally carried out at an elevated temperature, for example, between 80° C. and 140° C., conveniently at about 100° C.

It will be appreciated that a similar nucleophilic substitution reaction may be used for the preparation of compounds wherein V is an oxygen or sulfur atom, using an alcohol or thiol instead of the amine of formula (V). For the preparation of such ethers or thioethers, a suitable base will be required.

Compounds wherein V is a sulfur atom may be oxidized to corresponding compounds wherein V is SO or SO$_2$ using conventional methodology, for instance, oxone and wet alumina.

Further details of suitable procedures will be found in the accompanying Examples.

Compounds of formulae (II) and (V) are either known compounds or may be prepared by conventional methodology well known to one of ordinary skill in the art using, for instance, procedures described in the accompanying Examples, or by alternative procedures which will be readily apparent.

Compounds of formula (III) in which W is N, X is CH and Y is N (i.e. pyrimidines) may be prepared by the reaction of a compound of formula (VI) with a compound of formula (VII):

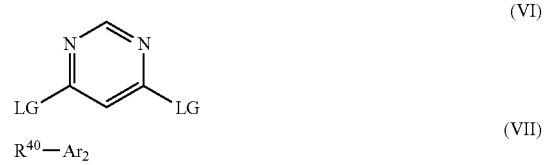

(VI)

(VII)

wherein LG is as previously defined and R$^{40}$ is B(OH)$_2$ or Sn(alkyl)$_3$, for example Sn(methyl)$_3$ or Sn(n-butyl)$_3$. Where R$^{40}$ is B(OH)$_2$, the reaction is conveniently effected under conditions suitable for a Suzuki Coupling Reaction (for review, see for instance A. Suzuki, Pure Appl. Chem., 1991, 63, 419-422), for example, in the presence of a palladium catalyst such as tetrakis(triphenylphosphine)palladium (0), (1,1'-bis(diphenylphosphino)ferrocene)dichloropalladium or dichloro-(1,4-bis(diphenylphosphino)butane)palladium, in a suitable solvent such as an ether, for example, dimethoxyethane or dioxane or an aromatic hydrocarbon, for example toluene, at an elevated temperature. Where R$^{40}$ is Sn(alkyl)$_3$, the reaction is conveniently effected under conditions suitable for a Stille Coupling Reaction (for review, see for instance J. K. Stille, Angew. Chem. Int Ed., 1986, 25, 508-524), for example, in the presence of a palladium catalyst such as tetrakis(triphenylphosphine)palladium (0) or bis(triphenylphosphine)palladium (II) chloride, in a suitable solvent such as an ether, for example dioxane, or an aromatic hydrocarbon, for example, toluene, at an elevated temperature. The reaction can be carried out at about 170° C. for about 10 minutes in a microwave.

Compounds of formula (III) in which W is N, X is CH and Y is CH (i.e. pyridines) may be prepared by the reaction of a compound of formula (VIII)

(VIII)

with a reagent suitable for the introduction of a leaving group. For instance, when LG is chlorine, by reaction with phosphorous oxychloride at an elevated temperature.

Similarly, compounds of formula (III) in which W is N, X is N and Y is CH (i.e. pyridazines) may be prepared by the reaction of a compound of formula (IX)

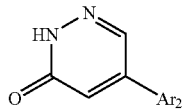
(IX)

with a reagent suitable for the introduction of a leaving group. For instance, when LG is chlorine, by reaction with phosphorous oxychloride at an elevated temperature.

Compounds of formulae (VIII) and (IX) may be prepared by reaction of a compound of formula (VII) with a compound of formula (X) or (XI), respectively:

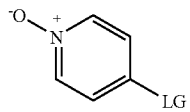
(X)

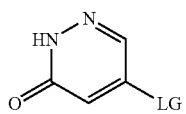
(XI)

using, for example, the Suzuki Coupling or Stille Coupling reaction conditions described above.

It will be appreciated that whilst the leaving group in the above coupling reactions is depicted on the compounds of formulae (VI), (X) and (XI), it may be desirable in certain circumstances to have the leaving group on the $Ar_2$ intermediate, and for the central heteroaromatic ring to be substituted by the $B(OH)_2$ or $Sn(alkyl)_3$ moiety.

Compounds of formulae (VI), (X and (XI) are either known compounds or may be prepared by conventional methodology well known to one of ordinary skill in the art using, for instance, procedures described in the accompanying Examples, or by alternative procedures which will be readily apparent.

Trisubstituted pyridines of formula (III) in which W is N, X is CH and Y is CH, and $R^2$ is other than hydrogen may be prepared using an iridium catalysed borylation reaction of a 2,6-disubstituted pyridine, or a method analogous thereto, as depicted in Scheme 1:

Scheme 1

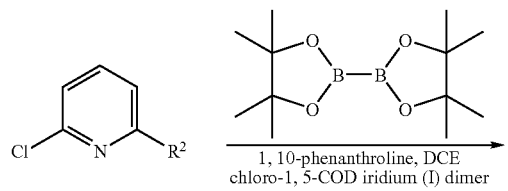

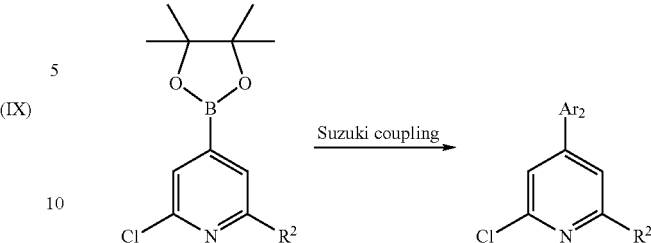

According to a further general process (C), compounds of formula (I) may be prepared by reaction of a compound of formula (VII) wherein $R^{40}$ is as defined above with a compound of formula (XII) in which $Ar_2$ is absent:

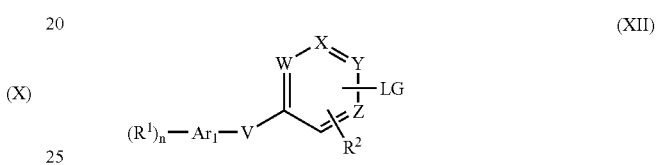
(XII)

in which $R^1$, $Ar_1$, n, V, X, Y, Z and $R^2$ are as defined for formula (I) and LG is a leaving group such a chlorine, under conditions suitable for a Suzuki coupling as described above.

Compounds of formula XII can be made by general process (A) in which the compound of formula (III) possesses an extra leaving group in place of $Ar_2$.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following non-limiting Examples serve to illustrate the preparation of compounds of the present invention. The structures of the products of the following Descriptions and Examples were in most cases confirmed by $^1$H NMR.

Description 1: 3-Methyl-5-nitroisoquinoline

3-Methylisoquinoline (2.14 g, 14.9 mmol) was added portionwise to ice-cooled concentrated $H_2SO_4$ (10 ml) keeping the internal temperature below 10° C. A nitrating mixture of concentrated $H_2SO_4$ (2 ml) and fuming nitric acid (2 ml) was then added dropwise keeping the internal temperature below 15° C. After stirring for 30 minutes, TLC indicated reaction was complete. The acid was neutralized by adding the mixture to an excess of 4N aqueous NaOH (180 ml) with ice-cooling. The mixture was extracted with dichloromethane (2×150 ml), then dried ($Na_2SO_4$) and evaporated to give the crude product (2.69 g) as a yellow solid. Flash column chromatography using as eluant 5% methanol in dichloromethane gave a pure sample of the title compound (660 mg) and a sample (1.95 g) containing ca. 10% of the 8-nitro isomer.

Description 2: 3-Methylisoquinolin-5-amine

Description 1 (660 mg, 3.51 mmol) was dissolved in MeOH (30 ml) and $PtO_2$ catalyst (120 mg) was added. The mixture was stirred for 1 hour 45 minutes under a balloon of hydrogen, then the catalyst was filtered off, washing with more methanol. The filtrate was evaporated and purified by flash column chromatography using as eluant 5% methanol in dichloromethane to give the title compound (250 mg). m/z ($ES^+$) 159 ($M+H^+$).

Description 3: 1-Methyl-5-nitroisoquinoline

Prepared by nitration of 1-methylisoquinoline according to the procedure of Description 1.

Description 4: 1-Methylisoquinolin-5-amine

Prepared by reduction of Description 3 according to the procedure of Description 2.

Description 5: 5,6,7,8-Tetrahydroisoquinolin-5amine

To a solution of 7,8-dihydroisoquinolin-5-(6H)-one oxime [*Synth. Commun.*, 26(12), 2305-2308, (1996)] (1 g, 6.2 mmol) in ethanol (20 ml) and ethyl acetate (1 ml) was added 10% palladium on carbon (250 mg). The resulting slurry was stirred under a hydrogen balloon at room temperature for 20 hours. The catalyst was removed by filtration and the solvent evaporated to give the title compound as a brown oil (953 mg, 100%). m/z ($ES^+$) 149 ($M+H^+$).

Description 6: 2,4-Difluoro-6-methoxybenzaldehyde

To a solution of 3.5-difluoroanisole (25 g, 175 mmol) in dichloromethane (150 ml) cooled at 0° C. was added titanium tetrachloride (30.7 ml, 280 mmol). To this mixture was added dropwise over 10 minutes dichloromethyl methylether (15.8 ml, 175 mmol), and after complete addition the mixture was stirred at room temperature for 1 hour. The reaction was poured onto ice/water (500 ml) and extracted with DCM (3×300 ml). The combined DCM layers were washed with water (500 ml), saturated NaCl (200 ml), dried over $Na_2SO_4$, filtered and evaporated. The residue was purified by column chromatography on silica-eluting with a gradient rising from 15% $Et_2O$ in isohexanes rising to 30% $Et_2O$ in isohexanes to give the title compound (11.2 g, 37%) as a white solid.

Description 7: 2,4-Difluoro-6-hydroxybenzaldehyde

To a solution of Description 6 (11.2 g, 77.8 mmol) in anhydrous dichloromethane (500 ml) cooled at −78° C. was added boron tribromide (9.47 ml; 85.58 mmol) dropwise over 10 minutes. After complete addition the mixture was allowed to warm to room temperature and stirred overnight. The mixture was poured onto ice/water (1 l) and extracted with DCM (3×400 ml). The combined organic layers were washed with water (1 l), saturated NaCl (500 ml), dried over $Na_2SO_4$, filtered and evaporated. The residue was purified by column chromatography on silica elution with 10% diethyl ether/isohexanes to give the title compound (9.2 g, 75%) as an orange oil.

Description 8: 2,4-Difluoro-6-prop-1-ynylbenzaldehyde

To an ice-bath cooled mixture of Description 7 (9.20 g, 58.2 mmol) and triethylamine (8.92 ml, 64.02 mmol) in anhydrous dichloromethane (100 ml) was added dropwise over 10 minutes trifluoromethanesulfonic anhydride (11.75 ml, 69.84 mmol) and the resulting mixture stirred at room temperature for 1 hour. The mixture was washed with water (300 ml), and the aqueous phase extracted with DCM (100 ml). The combined organic layers were washed with saturated NaCl (100 ml), dried over $Na_2SO_4$, filtered through a 1 inch plug of silica and evaporated. The residue (14.4 g, 49.6 mmol) and triethylamine (10.37 ml, 74.4 mmol) in anhydrous N,N-dimethylformamide (80 ml) contained within a large (200 ml capacity) sealed tube was cooled to −78° C. and propyne gas bubbled through until the volume had increased by approx 10 ml. To this mixture was added $Pd(PPh_3)_2Cl_2$ (1.74 g, 2.48 mmol) and CuI (449 mg, 4.96 mmol), the lid was put in place and the tube allowed to reach room temperature. The reaction was stirred for 2 hours after which TLC showed reaction was complete. The mixture was poured onto water (500 ml) and extracted with EtOAc (3×150 ml); the combined EtOAc layers were washed with water (3×400 ml), saturated NaCl (150 ml), dried over $Na_2SO_4$, filtered through a 1 inch plug of silica and evaporated to give the title compound (8.7 g, 97%).

Description 9: 6,8-Difluoro-3-methylisoquinoline

A mixture of Description 8 (8.7 g, 48.8 mmol) and 2.0M ammonia in methanol (244 ml, 488 mmol) were heated together at 80° C. in a Parr apparatus (approx 35 psi achieved) for 5 hours. The cooled mixture was evaporated and the residue purified by column chromatography on silica-elution with 100% dichloromethane to give the title compound (5.2 g, 59%) as a brown solid. $^1$H NMR (400 MHz, $CDCl_3$) δ 2.69 (3H, s), 6.93-6.99 (1H, m), 7.13 (1H, dd, J 9.1 and 1.4), 7.44 (1H, br s), 9.40 (1H, br s).

Description 10: 6,8-Difluoro-3-methylisoquinolin-5-amine

To an ice-bath cooled solution of Description 9 (1.2 g, 5.35 mmol) in conc. sulfuric acid (7.5 ml) was added dropwise a mixture of fuming nitric acid (1 ml) and conc. sulfuric acid (1 ml) and the resulting mixture stirred at 0° C. for 30 minutes. Poured onto ice/water (100 ml) and basified by the portionwise addition of $NaHCO_3$, then extracted with EtOAc (3×100 ml). The combined EtOAc layers were flushed with nitrogen and a spatula end of 5% palladium on carbon added and the reaction was stirred under a balloon of hydrogen for 3 hours. The catalyst was removed by filtration and the filtrate evaporated. The residue was purified by column chromatography on silica elution with 1% MeOH in DCM+0.5% $NH_4OH$ to give the title compound (930 mg, 89%).

Description 11: 3-Methyl-7-(trifluoromethyl)isoquinolin-5-amine

Prepared using 2-hydroxy-5-trifluoromethylbenzaldehyde [see WO-A-9962902] in place of 2,4-difluoro-6-hydroxybenzaldehyde according to the procedures of Descriptions 8, 9, and 10 respectively.

Description 12: 2-Fluoro-6-prop-1-ynylbenzaldehyde

A mixture of 2-bromo-6-fluorobenzaldehyde [see *Tetrahedron Letters* (1992), 33(49), 7499-7502] (4.0 g, 19.7 mmol) and triethylamine (4.12 ml, 29.5 mmol) in anhydrous N,N-dimethylformamide (75 ml) contained within a large (200 ml capacity) sealed tube was cooled to −78° C. and propyne gas bubbled through until the volume had increased by approx 10 ml. To this mixture was added $Pd(PPh_3)_2Cl_2$ (0.69 g, 0.99 mmol) and CuI (180 mg, 1.97 mmol), the lid was put in place and the tube allowed to reach room temperature and stir for 4 hours after which TLC showed the reaction was complete. The mixture was poured onto water (500 ml) and extracted with EtOAc (3×150 ml). The combined EtOAc layers were washed with water (3×400 ml), saturated NaCl (150 ml), dried over $Na_2SO_4$, filtered through a 1 inch plug of silica and evaporated to give the title compound (3.2 g, 100%).

Description 13:
8-Fluoro-3-methylisoquinolin-5-amine

Prepared using Description 12 in place of 2,4-difluoro-6-prop-1-ynylbenzaldehyde according to the procedures of Descriptions 9 and 10 respectively.

Description 14: (2-Bromo-4-fluorophenyl)methanol

To a solution of 2-bromo-4-fluorobenzoic acid (20 g, 91 mmol) in anhydrous THF (300 ml) at −10° C. was added dropwise borane tetrahydrofuran complex (1.0M soln in THF) (136.5 ml, 136.5 mmol). After complete addition the reaction was allowed to stir at room temperature for 4 hours. The reaction was quenched by the dropwise addition of water (20 ml). To the mixture was added saturated $K_2CO_3$ (200 ml) and water (300 ml). The organic layer was separated and the aqueous extracted with $Et_2O$ (2×300 ml). The combined organics were washed with water (2×500 ml), saturated NaCl (200 ml), dried over $Na_2SO_4$, filtered and evaporated to give the title compound (18 g, 96%) as a white solid.

Description 15: 2-Bromo-4-fluorobenzaldehyde

To a −78° C. cooled solution of oxalyl chloride (8.43 ml, 96.58 mmol) in anhydrous dichloromethane (300 ml) was added dropwise dimethyl sulfoxide (13.71 ml, 193.16 mmol). The mixture was stirred at −78° C. for 5 minutes then a solution of Description 14 (18 g, 87.8 mmol) in anhydrous dichloromethane (150 ml) was added slowly. The resulting mixture was stirred at −78° C. for 15 minutes then triethylamine (36.71 ml, 263.4 mmol) was added and the mixture allowed to warm to room temperature over 1 hour. The mixture was washed with water (2×500 ml), saturated NaCl (200 ml), dried over $Na_2SO_4$, filtered through a 2 inch plug of silica gel and evaporated to give the title compound (16 g, 89%) as a white solid.

Description 16:
6-Fluoro-3-methylisoquinolin-5-amine

Prepared using Description 15 in place of 2-bromo-6-fluorobenzaldehyde according to the procedures of Descriptions 12, 9, and 10 respectively.

Description 17: 1-Methyl-5-nitroquinolinium iodide

5-Nitroquinoline (4 g, 30 mmol) was melted at 85° C., prior to addition of dimethyl sulfate (2.2 ml, 30 mmol), and the resulting mixture was stirred at this temperature for 1.5 hours. The yellow gel was dissolved in water (35 ml) and cooled to room temperature. A saturated aqueous solution of potassium iodide (7.63 g, 45.9 mmol) was added, and the resulting orange precipitate was filtered, washing the residue with chilled water. After drying under vacuum at 60° C., for 2 hours, the brick-red solid was used in the next step without purification.

Description 18: 1-Methyl-5-nitroquinolin-2(1H)-one

Description 17 (3.53 g, 11.2 mmol), and potassium hexacyanoferrate(III) (8.11 g, 24.7 mmol) were suspended in water (ca. 30 ml) and THF (ca 30 ml), and the mixture was basified to pH 14 with 4N NaOH (aq), and stirred for a further 48 hours. After concentrating to dryness and the residue was partitioned between DCM/water and filtered through Celite™, washing the filter pad with DCM (200 ml) and water (100 ml). The organic phase was dried over sodium sulfate and concentrated to give a dark brown oil. Purification by flash chromatography gave a pale brown solid. (1.15 g, 50%). m/z ($ES^+$) 205 ($M+H^+$).

Description 19:
5-Amino-1-methyl-3,4-dihydroquinolin-2(1H)-one

Description 18 (200 mg, 0.98 mmol) was dissolved in acetic acid (25 ml) and hydrogenated over $PtO_2$ (11 mg) at 60 psi. The catalyst was removed by filtration, and the filtrate was concentrated to give a colourless gel, which was partitioned between $CHCl_3$ (30 ml)/saturated aqueous $NaHCO_3$ (30 ml). The aqueous phase was extracted with $CHCl_3$ (3×30 ml), dried $Na_2SO_4$) and concentrated under reduced pressure to give a white solid (120 mg, 70%). m/z ($ES^+$) 177 ($M+H^+$).

Description 20:
5-Amino-1-methylquinolin-2(1H)-one

Description 18 (0.42 g, 2.06 mmol) and tin(II) chloride dihydrate (2.09 g, 9.26 mmol) were suspended in ethanol (20 ml), and the mixture was heated to reflux for 16 hours. The volatiles were removed under reduced pressure and the residue was suspended in water (30 ml) and the pH was adjusted to 8 with 4M NaOH (aq). The mixture was extracted with chloroform (4×50 ml), the combined organic extracts were dried ($Na_2SO_4$) and concentrated to give a cream-colored solid (0.32 g, 89%). m/z ($ES^+$) 175 ($M+H^+$).

Description 21: 1-Methyl-4-nitro-1H-indazole and 2-methyl-4-nitro-2H-indazole To a solution of 4-nitro indazole [WO-A-0135947] (5.0 g, 31 mmol) in dimethylformamide at 0° C. was added sodium hydride (1.34 g of a 60% dispersion in oil, 34 mmol). The mixture was stirred at room temperature for 10 minutes. Iodomethane (2.28 ml, 37 mmol) was added and the reaction stirred at room temperature for 90 minutes. Water (500 ml) was added and the reaction extracted into ethyl acetate (3×200 ml). The combined organic layers were washed with water (2×200 ml) then dried ($Mg_2SO_4$) and evaporated. Trituration overnight in dichloromethane/hexane gives 0.97 g of pure 1-methyl-4-nitro-1H-indazole. The remaining solution was condensed and purified by column chromatography on silica eluting with 40-20% hexane in dichloromethane to give additional 1-methyl-4-nitro-1H-indazole (1.30 g, total 2.27 g, 42%) as the less polar product $^1$H NMR (360 MHz, $CDCl_3$) 4.18 (3H, s), 7.52 (1H, t, J 8.0), 7.77 (1H, d, J 8.4), 8.15 (1H, d, J 7.7), 8.61 (1H, s); and as the more polar, 2-methyl-4-nitro-2H-indazole (1.50 g, 28%). $^1$H NMR (400 MHz, $CDCl_3$) 4.32 (3H, s), 7.40 (1H, t, J 8.0), 8.07 (1H, d, J 8.6), 8.18 (1H, d, J 7.6), 8.55 (1H, s).

Description 22: 1-Methyl-1H-indazol-4-amine

To a solution of Description 21 (0.97 g, 5.5 mmol) in ethanol (50 ml) was added catalytic 10% palladium on carbon. The resulting slurry was stirred under a balloon of hydrogen for 2 hours. The catalyst was removed by filtration and the solvent evaporated and the product azeotroped with toluene to give the title compound as a pale brown solid (0.78 g, 96%). m/z ($ES^+$) 148 ($M+H^+$).

Description 23: 2-Methyl-2H-indazol-4-amine

Prepared from Description 21 according to the procedure of Description 22. m/z (ES$^+$) 148 (M+H$^+$).

Description 24: 4-Nitro-1-{[2-trimethylsilylethoxy]methyl}-1H-indazole

To a solution of 4nitroindazole (2.55 g, 15.6 mmol) in anhydrous dimethylformamide (20 ml) at room temperature was added sodium hydride (902 mg, 37.6 mmol, 2.4 eq, 60% dispersion in oil) portionwise. This was allowed to stir at room temperature for 10 minutes. 2-(Chloromethoxy)ethyl-trimethylsilane (3.3 ml, 18.8 mmol, 1.2 eq) was added and the reaction stirred at room temperature for a further 90 minutes. Water (30 ml) was added and the reaction extracted into diethyl ether (2×50 ml). The combined organic layers were washed with brine (2×50 ml), the layers separated and the organic layer dried over MgSO$_4$, filtered and evaporated. The resulting oil was purified by column chromatography on silica eluting with 20% ethyl acetate in isohexane, to give 4-nitro-1-{[2-trimethylsilylethoxy]methyl}-1H-indazole (1.74 g, 38%) as the less polar product and 4-nitro-2-{[2-trimethylsilylethoxy]methyl}-2H-indazole (1.93 g, 42%) as the more polar product. $^1$H NMR—1-Substituted isomer—(360 MHz, CDCl$_3$) δ 0.00 (9H, s), 0.94 (2H, t, J 8.4), 3.63 (2H, t, J 8.2), 5.89 (2H, s), 7.62 (1H, t, J 8.0), 8.03 (1H, d, J 8.3), 8.26 (1H, d, J 7.7), 8.71 (1H, s).

Description 25: 1-{[2-Trimethylsilylethoxy]methyl}-1H-indazol-4-amine

To a solution of Description 24 (1.74 g, 5.9 mmol) in ethanol (25 ml) was added 10% palladium on carbon (190 mg). The resulting slurry was hydrogenated at 50 psi for 1 hour. The reaction was filtered and the solvent evaporated to give the title compound as a brown oil (1.55 g, 99% yield). m/z (ES$^+$) 264 (M+H$^+$)

Description 26: Methyl 5-fluoro-2-methyl-3-nitrobenzoate

To a solution of 5-fluoro-2-methyl benzoic acid (62.6 g, 406 mmol) in conc. sulfuric acid (500 ml) cooled at −10° C. was added dropwise a mixture of fuming nitric acid (20.6 ml) and conc. sulfuric acid (94 ml). After complete addition the mixture was stirred at 0° C. for 1 hour. Poured onto ice/water (1.5 l) and stirred for 10 minutes then extracted with EtOAc (3×500 ml), the combined EtOAc layers were washed with water (800 ml), saturated NaCl (500 ml), dried over Na$_2$SO$_4$, filtered and evaporated. The residue was dissolved in methanol (1 l) and conc. HCl (15 ml) added, and the resulting mixture heated at reflux overnight. The cooled reaction mixture was evaporated and the residue partitioned between DCM (700 ml) and saturated NaHCO$_3$, the organic layer was separated and washed with saturated NaCl (200 ml), dried over Na$_2$SO$_4$, filtered and evaporated to give the title compound (51.5 g, 59%) as an oil.

Description 27: Methyl 3-amino-5-fluoro-2-methylbenzoate

To a nitrogen flushed solution of Description 26 (51.58 g, 242 mmol) in methanol (400 ml) was added 5% Palladium on carbon (3 g), and the resulting mixture hydrogenated on a Parr apparatus at 50 psi until hydrogen uptake ceased (approx 45 minutes). The catalyst was removed by filtration and the filtrate evaporated to dryness to give the title compound (39.5 g, 89%) as a solid.

Description 28: Methyl 6-fluoro-1H-indazole-4-carboxylate

To a mixture of Description 27 (39.5 g, 216 mmol) and ammonium tetrafluoroborate (30.12 g, 287.3 mmol) in a mixture of water (400 ml) and conc. hydrochloric acid (60 ml) cooled in an ice bath, was added a solution of sodium nitrite (14.9 g, 216 mmol) in water (60 ml). After complete addition the mixture was stirred for 40 minutes. The precipitate was filtered and washed with diethyl ether. This solid was then added in one portion to a mixture of potassium acetate (23.32 g, 237.6 mmol), and 18-crown-6 (1.71 g, 6.48 mmol) in chloroform (800 ml), and the resulting mixture stirred at room temperature for 1 hour. Water (500 ml) was added and the layers separated; the aqueous was further extracted with dichloromethane (2×300 ml), and the combined organic layers washed with water, saturated NaCl, dried over Na$_2$SO$_4$, filtered and evaporated. The residue was triturated with isohexanes, filtered and dried to give the title compound (11.5 g, 27%) as an orange solid.

Description 29: Methyl 6-fluoro-1-methyl-1H-indazole-4-carboxylate

To a solution of Description 28 (5.00 g, 25.8 mmol) in anhydrous N,N-dimethylformamide (75 ml) was added sodium hydride (60% dispersion in oil) (1.2 g, 30.96 mmol) followed 5 minutes later by iodomethane (1.93 ml, 30.96 mmol), and the resulting mixture stirred at room temperature overnight. Poured into water (500 ml) and extracted with EtOAc (3×100 ml); the combined EtOAc layers were washed with water (3×200 ml), saturated NaCl (100 ml), dried over Na$_2$SO$_4$, filtered and evaporated. The residue was purified by column chromatography on silica eluting with a gradient rising from 25% EtOAc in isohexanes to 50% EtOAc in isohexanes to give the title compound (2.62 g, 48%).

Description 30: 6-Fluoro-1-methyl-1H-indazole-4-carboxylic Acid

To a solution of Description 29 (2.62 g, 12.6 mmol) in methanol (50 ml) was added a solution of sodium hydroxide (2.52 g, 63 mmol) in water (20 ml) and the resulting mixture heated at reflux overnight The mixture was cooled and the methanol removed by evaporation. Water (100 ml) was added and then the mixture was acidified by the addition of conc. HCl, and extracted with EtOAc (3×75 ml); the combined EtOAc layers were washed with water (100 ml), saturated NaCl (50 ml), dried over Na$_2$SO$_4$, filtered and evaporated to give the title compound (1.8 g, 74%) as a yellow solid.

Description 31: tert-Butyl 6-fluoro-1-methyl-1H-indazol-4-ylcarbamate

To a solution of Description 30 (2.33 g, 12 mmol) in anhydrous toluene (50 ml) was added triethylamine (1.84 ml, 13.2 mmol) followed by diphenylphosphoryl azide (2.85 ml, 13.2 mmol) and the resulting mixture heated to reflux for 1 hour. After this time 2-methyl-2-propanol (1.7 ml, 18.0 mmol) was added and heating continued overnight. The mixture was cooled and evaporated, and the residue purified by column chromatography on silica elution with 50% diethyl ether in isohexanes to give the title compound (1.82 g, 57%).

Description 32: 6-Fluoro-1-methyl-1H-indazol-4-amine

A solution of Description 31 (1.82 g, 6.86 mmol) in anhydrous methanol (50 ml) was saturated with hydrogen chloride gas and left standing until HPLC showed complete reaction. The mixture was evaporated and the residue partitioned between saturated NaHCO$_3$ and DCM. The organic layer was separated and washed with saturated NaCl, dried over Na$_2$SO$_4$, filtered and evaporated to give the title compound (940 mg, 83%).

Description 33: 1-Methyl-6-trifluoromethyl-1H-indazol-4-amine

Prepared from 2-methyl-5-trifluoromethyl benzoic acid in place of 5-fluoro-2-methyl benzoic acid using analogous procedures to those described in Descriptions 26 to 32 respectively.

Description 34: Ethyl 2-cyanonicotinate

To ethyl 2chloronicotinate (15.0 g, 81 mmol) in anhydrous N,N-dimethylacetamide (75 ml) was added zinc cyanide (5.71 g, 48.6 mmol), Pd$_2$(dba)$_3$ (742 mg, 0.81 mmol), zinc (636 mg, 9.72 mmol), and 1,1'bis(diphenylphosphino)ferrocene (898 mg, 1.62 mmol), and the resulting mixture heated at 120° C. for 1 hour. The mixture was cooled to room temperature and partitioned between water (300 ml) and diethyl ether (150 ml), the mixture was filtered through Celite™ and the phases separated. The aqueous phase was further extracted with diethyl ether (2×100 ml), the combined diethyl ether layers washed with saturated NaCl, dried over Na$_2$SO$_4$, filtered and evaporated to give the title compound (14.26 g, 100%).

Description 35: [3-Ethoxycarbonylpyridin-2-yl]methanaminium chloride

To a nitrogen flushed solution of Description 34 (14.27 g, 81 mmol) and conc. HCl (15 ml) was added 10% Palladium on carbon (2 g), and the resulting mixture hydrogenated at 50 psi until HPLC and MS indicated complete conversion (approx 2 days). The catalyst was removed by filtration and the filtrate evaporated to give the title compound (17.55 g, 100%).

Description 36: Ethyl imidazo[1,5-a]pyridine-8-carboxylate

Acetic anhydride (38.21 ml, 405 mmol) and formic acid (15.28 ml, 405 mmol) were mixed together at 60° C. for 2 hours then allowed to cool to room temperature. To this mixture was added Description 35 (17.55 g, 81 mmol), and the resulting mixture stirred at room temperature for 1 hour, then heated at 35° C. for 3 hours. The mixture was cooled to 5° C. and neutralised with 0.88 ammonia solution and then extracted with dichloromethane (3×). The combined dichloromethane layers were washed with water, saturated NaCl, dried over Na$_2$SO$_4$, filtered and evaporated. The residue was purified by column chromatography on silica eluting with 2% MeOH in DCM+0.5% NH4OH to give the title compound (8.67 g, 56%).

Description 37: Imidazo[1,5-a]pyridine-8-carboxylic Acid

Description 36 (8.67 g, 45.6 mmol) and KOH [1,0M in methanol] (91.2 ml, 91.2 mmol) were mixed together and heated to reflux for 30 minutes when HPLC indicated the reaction was complete. The mixture was cooled and evaporated to dryness. Water (50 ml) was then added, and the mixture acidified with 2N HCl to give a yellow precipitate. The precipitate was filtered and washed successively with water, ethanol, and diethyl ether to give the title compound (3.1 g, 42%) as a yellow solid.

Description 38: tert-Butyl imidazo[1,5-a]pyridin-8-ylcarbamate

To a suspension of Description 37 (2.0 g, 12.31 mmol) and triethylamine (1.89 ml, 13.54 mmol) in anhydrous toluene (75 ml) was added diphenylphosphoryl azide (2.92 ml, 13.54 mmol), and the resulting mixture heated at reflux for 1 hour. To this mixture was added 2-methyl-2-propanol (1.74 ml, 18.47 mmol) and heating continued overnight The mixture was cooled and evaporated, and the residue purified by column chromatography on silica elution with 4% MeOH in DCM+0.5% NH4OH to give the title compound (1.85 g, 64%) as a white solid.

Description 39: Imidazo[1,5-a]pyridin-8-amine

A solution of Description 38 (1.00 g, 4.29 mmol) in anhydrous methanol (50 ml) was saturated with hydrogen chloride gas. The mixture was left standing for 2 hours—HPLC indicated reaction was complete. The mixture was evaporated and the residue basified by the addition of saturated NaHCO$_3$. The mixture was extracted with DCM (3×75 ml), and the combined DCM layers washed with saturated NaCl, (50 ml), dried over Na$_2$SO$_4$, filtered and evaporated to give the title compound (423 mg, 74%) as a dark solid.

Description 40: tert-Butyl 2-4-methylphenylsulfonyl-hydrazonomethyl)pyridin-3-ylcarbamate To a solution of tert-butyl 2-formylpyridin-3-ylcarbamate (4.4 g, 20 mmol) (*Tetrahedron*, 54, (1998), 6311-6318) in methanol (90 ml) was added p-toluenesulfonyl hydrazide (3.7 g, 20 mmol). The solution was heated to reflux for 5 minutes and allowed to cool to room temperature. A white solid was seen to precipitate out which was collected by filtration to give the title compound (6.6 g, 85%).

Description 41: tert-Butyl [1,2,3]triazolo[1,5-a]pyridin-4-ylcarbamate

A solution of the p-toluenesulfonyl hydrazone derived from Description 40 (6.6 g, 17 mmol) in morpholine (75 ml) was heated at reflux for 90 minutes. The cooled reaction mixture was evaporated and the residue partitioned between ethyl acetate (50 ml) and saturated sodium bicarbonate solution (75 ml). The aqueous phase was extracted with ethyl acetate (2×50 ml). The combined organic extracts were washed with brine (50 ml), dried over MgSO$_4$, filtered and evaporated. The residue was purified by flash column chromatography using eluant system of 1:1 ethyl acetate:hexane to give the title compound (1.1 g, 28%).

Description 42:
[1,2,3]Triazolo[1,5-a]pyridin-4-amine

To an ice-cooled solution of Description 41 (1.1 g, 4 mmol) in dichloromethane (10 ml) was added trifluoroacetic acid (10 ml). The reaction mix was warmed to room temperature and stirred for 2 hours. The reaction mixture was then evaporated and partitioned between saturated sodium bicarbonate solution and ethyl acetate. The organic layer was evaporated to give the title compound (480 mg, 75%).

Description 43:
2-Chloro-4-[4-trifluoromethylphenyl]pyridine

To a mixture of 4-chloropyridine-N-oxide (5.32 g, 41 mmol) and 4-trifluoromethylphenylboronic acid (9.36 g, 49.3 mmol) in anhydrous 1,2-dimethoxyethane (100 ml) was added tetrakis(triphenylphosphine)palladium (0) (1.5 g, 1.3 mmol) and saturated aqueous sodium carbonate solution (50 ml). Nitrogen was bubbled through the mixture for 5 minutes and the reaction was then heated with stirring at 100° C. for 15 hours under an atmosphere of nitrogen. The mixture was allowed to cool to room temperature and the solid was filtered off and washed with 1,2-dimethoxyethane (2×30 ml). The combined organic layers were evaporated under reduced pressure and triturated with diethyl ether (100 ml). The obtained solid was filtered off and dried on the sinter to give 4-(4-trifluoromethylphenyl)pyridine-N-oxide (8.36 g). This compound was suspended in phosphorous oxychloride (50 ml, 536 mmol) and the mixture was heated at 100° C. for 3 hours. After cooling to room temperature the homogeneous dark solution was evaporated under reduced pressure and repartitioned between chloroform and water (200 ml each). The pH was adjusted to 8 by portionwise addition of saturated aqueous sodium carbonate solution and the phases were separated. After two further extractions the combined organic extracts were washed with water and brine and dried over sodium sulfate. After filtration the compound was adsorbed onto silica gel and purified by flash chromatography (10% ethyl acetate-iso-hexane) to yield the title compound (5.5 g, 52%).

Description 44:
2-Chloro-4-[4-trifluoromethoxyphenyl]pyridine

Prepared from 4-chloropyridine-N-oxide and 4-trifluoromethoxyphenylboronic acid according to the procedure of Description 43, (0.22 g, 44%).

Description 45:
2-Chloro-4-[3-trifluoromethylphenyl]pyridine

Prepared from 4-chloropyridine-N-oxide and 3-trifluoromethylphenylboronic acid according to the procedure of Description 43, (1.2 g, 60%).

Description 46: 2-Chloro-4-phenylpyridine

Prepared from 4-chloropyridine-N-oxide and phenylboronic acid according to the procedure of Description 43, (3.13 g, 45%).

Description 47: 2,6-Dichloro-4(4,45,5-tetramethyl-1,3,2-dioxaborolan-2-yl)pyridine To a mixture of 2,6-dichloropyridine (3.28 g, 22.2 mmol) and bis(pinacolato)diboron (6.2 g, 24.4 mmol) was added 1,10-phenanthroline (0.24 g, 1.3 mmol) and chloro-1,5-cyclooctadiene iridium (I) dimer (0.44 g, 0.66 mmol) under nitrogen followed by anhydrous 1,2-dichloroethane. Nitrogen was bubbled through the mixture for 5 minutes and the reaction was then heated with stirring at 100° C. for 15 hours under an atmosphere of nitrogen. The mixture was allowed to cool to room temperature, poured onto diethylether/4N sodium hydroxide (50 ml 200 ml) and the phases separated. The aqueous phase was acidified with 6N hydrochloric acid and the resulting solid was filtered, washed with water and dried on the sinter to yield the pinacol ester of 2,6-dichloropyridin-4-ylboronic acid (3.5 g, 58%) as a grey solid.

Description 48:
2,6-Dichloro-4-[4-trifluoromethylphenyl]pyridine

To a mixture of the pinacol ester of Description 47 (1.0 g, 3.65 mmol) and 4-iodobenzotrifluoride (2.0 g, 7.35 mmol) in anhydrous dioxane (25 ml) was added (1,1'-bis(diphenylphosphino)ferrocene)-dichloropalladium (0.14 g, 1.91 mmol) and saturated aqueous sodium carbonate solution (4 ml). Nitrogen was bubbled through the mixture for 5 minutes and the reaction was then heated with stirring at 90° C. for 15 hours under an atmosphere of nitrogen. The mixture was allowed to cool to room temperature and poured onto a mixture of ethyl acetate/water (100 ml/30 ml). The phases were separated and the aqueous phase was extracted two times more with ethyl acetate. The combined organic layers were washed with brine, dried over sodium sulfate and adsorbed onto silica gel. Purification by flash chromatography (10% ethyl acetate-iso-hexane) yielded the title compound (0.59 g, 56%) as a white solid.

Description 49:
2,6-Dichloro-4-(pyridin-4-yl)pyridine

Prepared from the pinacol ester of Description 47 and 4-bromopyridine hydrochloride according to the procedure of Description 48 (4.9 g, 87%).

Description 50: 2-Chloro-methyl (4,4,5,5-tetramethyl-1,3,2-dioxaborolan-2-yl)pyridine Prepared from 2-chloro-6-methylpyridine and bis(pinacolato)diboron according to the procedure of Description 47 (4.8 g, 78%).

Description 51: 2-Chloro-6-methyl-4-[4-trifluoromethylphenyl]pyridine

Prepared from the pinacol ester of Description 50 and 4-iodobenzotrifluoride according to the procedure of Description 48 (2.64 g, 97%).

Description 52: 2-Chloro-6-methoxy-4-(4,4,5,5-tetramethyl-1,3,2-dioxaborolan-2-yl)pyridine Prepared from 2-chloro-6-methoxypyridine and bis(pinacolato)diboron according to the procedure of Description 47 (5.2 g, 79%).

Description 53: 2-Chloro-6-methoxy-[4-trifluoromethylphenyl]pyridine

Prepared from the pinacol ester of Description 52 and 4-iodobenzotrifluoride according to the procedure of Description 48 (2.2 g, 77%).

Description 54:
3-Chloro-5-[4-trifluoromethylphenyl]pyridazine

To a mixture of 5-chloropyridazin-3(2H)-one [ES-A-454136 (1977)] (2.32 g, 17.8 mmol) and 4-trifluoromethylphenylboronic acid (4.06 g, 21.4 mmol) in anhydrous dioxane (20 ml) was added (1,1'-bis(diphenylphosphino)ferrocene)-dichloropalladium (0.8 g, 1.09 mmol) and saturated aqueous sodium carbonate solution (18 ml). Nitrogen was bubbled through the mixture for 5 minutes and the reaction was then heated with stirring at 100° C. for 24 hours under an atmosphere of nitrogen. The mixture was allowed to cool to room temperature and poured onto a mixture of ethyl acetate/ethanol/water (300 ml/30 ml/30 ml). The phases were separated and the aqueous phase was extracted two times more with ethyl acetate. The combined organic layers were washed with brine, dried over sodium sulfate and adsorbed onto silica gel. Purification by flask column chromatography (50% ethyl acetate-iso-hexane) gave 5-[4-trifluoromethylphenyl]pyridazin-3(2H)-one (0.78 g) which was suspended in phosphorous oxychloride (5 ml, 54 mmol) and the mixture heated at 100° C. for 5 hours. After cooling to room temperature the homogeneous dark solution was evaporated under reduced pressure and repartitioned between chloroform and water (50 ml each). The pH was adjusted to 8 by portionwise addition of saturated aqueous sodium carbonate solution and the phases were separated. After two further extractions the combined organic extracts were washed with water and brine and dried over sodium sulfate. After filtration the compound was adsorbed onto silica gel and purified by flash column (50% ethyl acetate-iso-hexane) to yield the title compound (0.56 g, 12%).

Description 55:
5-(4-tert-Butylphenyl)pyridazin-3(2H)-one

A mixture of 5-chloropyridazin-3(2H)-one (2.94 g, 22.5 mmol), 4-tert-butylphenylboronic acid (8 g, 44.9 mmol), dioxane (100 ml), 2M aqueous sodium carbonate solution (25 ml) and [1,1'-bis(diphenylphosphino)-ferrocene]dichloropalladium (0.5 g) was degassed ($N_2$), then heated at 100° C. for 18 hours under nitrogen. After cooling to room temperature and standing 24 hours, ethyl acetate (250 ml) was added. The mixture was filtered and the collected solid washed with ethyl acetate to give the title compound 2.36 g. The layers of the filtrate were separated, the aqueous phase extracted with ethyl acetate (100 ml) and the combined organic phases evaporated. Ethyl acetate (100 ml) was added to the residue and the mixture left to stand. A second crop of crystals (2.26 g) was collected and washed with ethyl acetate, giving a combined yield of 4.62 g, 90%.

Description 56:
5-4-tert-Butylphenyl)-3-chloropyridazine

Description 55 (2.35 g, 9.53 mmol) was added to phosphorus oxychloride (20 ml) and the mixture heated at 85° C. for 1 hour. The cooled reaction mixture was cautiously added to ice-water (200 ml) and stirred for 10 minutes. The mixture was then extracted with ethyl acetate (2×100 ml) and the combined organic layers washed with 10% aqueous potassium carbonate solution (50 ml), then dried ($Na_2SO_4$) and evaporated. The residue was purified by flash column chromatography eluting with 15% ethyl acetate-hexane, increasing to 25% ethyl acetate-hexane to give the title compound (2.28 g, 90%).

Description 57:
5-(3-Cyanophenyl)pyridazin-3(2H)-one

To a mixture of 5-chloropyridazin-3(2H)-one (2.0 g, 15.3 mmol) and 3-cyanophenyl boronic acid (2.71 g, 18.4 mmol) in anhydrous toluene (20 ml) was added dichloro-(1,4-bis(diphenylphosphino)-butane)palladium (0.1 g, 0.16 mmol), and saturated aqueous sodium carbonate solution (5.0 ml) and the mixture was irradiated in a Milestone microwave reactor at 120° C. for 15 minutes. The resulting suspension was filtered and the solid was washed with isopropanol (20 ml) and dried on the sinter to give 5-(3-cyanophenyl)pyridazin-3-one (1.8 g, 50%) as a yellow solid.

Description 58:
3-Chloro-5-(3-cyanophenyl)pyridazine

Description 57 (1.8 g, 9.1 mmol) was suspended in phosphorous oxychloride (15 ml, 12 mmol) and the mixture was heated at 100° C. for 1 hour. After cooling to room temperature the homogeneous dark solution was concentrated under reduced pressure to ⅓ of its original volume poured onto ice-water (250 ml). The pH was adjusted to 8 by portionwise addition of saturated aqueous sodium carbonate solution and the resulting solid was filtered, washed with water and dried on the sinter to yield the title compound (1.5 g, 76%).

Description 59:
3,6-Dichloro-5-[4-trifluoromethylhenyl]pyridazine

4-Trifluoromethylphenylacetonitrile (38.9 g, 210 mmol) was dissolved in dry methanol under nitrogen. Glyoxylic acid monohydrate (29 g, 315 mmol) was added followed by potassium carbonate (74 g, 535 mmol) and the resulting mixture was stirred for 15 hours at room temperature. The resulting solid was filtered, washed with dichloromethane and dried on the sinter to yield an off white solid which was added at room temperature to a solution of conc. sulfuric acid (30 ml) and formic acid (400 ml). The resulting mixture was then heated with stirring at 110° C. for 3 hours, allowed to cool to room temperature and concentrated under vacuum to ⅔ of the initial volume. It was then poured ice-water (1000 ml) and the resulting solid was filtered off, washed with water and dried on the sinter to yield 35 g of 3-(4-trifluoromethylphenyl)maleic anhydride as an off white solid. The crude anhydride (35 g) was suspended in water (290 ml) and glacial acetic acid (145 ml) was added followed by a solution of hydrazine hydrate (7 ml, 144 mmol) in water (21 ml). After thorough mixing conc. sulfuric acid was added in small portions with external water cooling and the mixture was heated while stirring at 125° C. for 3 hours. After cooling to room temperature the solid was filtered off, washed with water until the pH was neutral and dried on the sinter to yield a grey solid. Phosphorous oxychloride (200 ml, 2.1 mol) was added to the solid and the mixture was heated at 120° C. for 2 hours. After cooling to room temperature the homogeneous dark solution was concentrated under reduced pressure to half of its original volume and poured into water (800 ml) while stirring vigorously. The resulting solid was filtered off, washed with water and dried on the sinter to yield a grey solid which was recrystallised from toluene/iso-hexane (1:1) to yield the title compound as a yellow solid (8.2 g, 13%).

Description 60:
3-Chloro-5-(3-methylpyridin-2-yl)pyridazine

To a mixture of 5-chloropyridazin-3(2H)-one (0.135 g, 1 mmol) and 2-(tri-n-butylstannyl)-3-methylpyridine (0.42 g, 1.1 mmol) in anhydrous 1,4-dioxane (2 ml) was added tetrakis(triphenylphosphine)-palladium (0) (0.06 g, 0.051 mmol), copper(I)iodide (20 mg, 0.1 mmol) and lithium chloride (0.13 g, 3.1 mmol) and the mixture was irradiated in a Smith microwave reactor at 160° C. for 15 minutes. The mixture was allowed to cool to room temperature and poured onto a mixture of ethyl acetate/water (10 ml/5 ml). The phases were separated and the aqueous phase was extracted two times more with ethyl acetate. The combined organic layers were washed with brine, dried over sodium sulfate and adsorbed onto silica gel. Purification by flash chromatography (ethyl acetate) gave 5-(3-methylpyrid-2-yl)pyridazin-3(2H)-one (0.13 g, 69%) as a yellow solid which was suspended in phosphorous oxychloride (5 ml, 54 mmol) and the mixture was heated at 100° C. for 1 hour. After cooling to room temperature the homogeneous dark solution was evaporated under reduced pressure and repartitioned between chloroform and water (50 ml each). The pH was adjusted to 8 by portionwise addition of saturated aqueous sodium carbonate solution and the phases were separated. After two further extractions the combined organic extracts were washed with water and brine and dried over sodium sulfate. After filtration the compound was adsorbed onto silica gel and purified by flash column (50% ethyl acetate-iso-hexane) to yield the title compound (0.38 g, 54%).

Description 61:
5-(4-Methoxyphenyl)pyridazin-3(2H)-one

Five reaction tubes each containing 5-chloropyridazin-3(2H)-one (100 mg, 0.77 mmol), 4-methoxyphenylboronic acid (230 mg, 1.53 mmol), dioxane (3 ml), 2M aqueous sodium carbonate solution (1 ml) and [1,1'-bis(diphenylphosphino)ferrocene] dichloropalladium (20 mg) were irradiated in a microwave reactor at 150° C. for 10 minutes. After cooling to room temperature the mixtures were combined and filtered. The collected solid was washed with water (3 ml), ethyl acetate (5 ml) and ether (5 ml), then dried to give the title compound (724 mg, 93%).

Description 62:
3-Chloro-5-(4-methoxyphenyl)pyridazine

Description 61 (720 mg, 3.56 mmol) was added to phosphorus oxychloride (10 ml) and the mixture heated at 100° C. for 16 hours. The cooled reaction mixture was cautiously added to ice-water (250 ml) and stirred for 10 minutes. The mixture was then extracted with dichloromethane (3×100 ml) and the combined organic layers washed with 10% aqueous potassium carbonate solution (100 ml), then dried ($Na_2SO_4$) and evaporated. The residue was purified by flash column chromatography eluting with 5% methanol in dichloromethane to give the title compound (483 mg).

Description 63: 5-[2-Fluoro-4-trifluoromethylphenyl]pyridazin-3(2H)-one

A mixture of 5-chloropyridazin-3(2H)-one (1.91 g, 14.6 mmol), bis(pinacolato)diboron (3.89 g, 15.3 mmol), potassium acetate (2.14 g, 21.8 mmol), dioxane (100 ml) and [1,1'-bis(diphenylphosphino)ferrocene]-dichloropalladium (0.4 g) was degassed ($N_2$), then heated at 90° C. for 16 hours under nitrogen. More catalyst (0.45 g) was added and the mixture heated 7 hours more. After cooling to room temperature 4-bromo-3-fluorobenzotrifluoride (4.5 g, 18.5 mmol) was added along with 2M aqueous sodium carbonate solution (35 ml) and a further portion of catalyst (450 mg). The mixture was heated to 115° C. for 24 h, then cooled to room temperature, diluted with ethyl acetate (250 ml) and filtered. The layers were separated, the aqueous phase extracted with ethyl acetate (100 ml) and the combined organic layers evaporated. The residue was purified by flash column chromatography eluting with 5% methanol in dichloromethane to give the title compound (795 mg, 21%).

Description 64: 3-Chloro-5-[2-fluoro-4-trifluoromethylphenyl]pyridazine

Description 63 (763 mg, 2.96 mmol) was added to phosphorus oxychloride (5 ml) and the mixture heated at 85° C. for 1 hour. The cooled reaction mixture was cautiously added to ice-water (75 ml) and stirred for 10 minutes. The mixture was then extracted with dichloromethane (2×50 ml) and the combined organic layers washed with half saturated aqueous sodium bicarbonate solution (50 ml), then dried ($Na_2SO_4$) and evaporated. The residue was purified by flash column chromatography eluting with 5% methanol in dichloromethane to give the title compound (420 mg, 51%).

Description 65:
5-Chloro-3-(4-fluorophenyl)pyridazine

To a mixture of S-chloropyridazin-3(2H)-one (7.33 g, 56 mmol) was suspended in phosphorous oxychloride (55 ml, 594 mmol) and the mixture was heated at 80° C. for 3 hours. After cooling to room temperature the homogeneous dark solution was evaporated under reduced pressure and repartitioned between chloroform and water (50 ml each). The pH was adjusted to 8 by portionwise addition of saturated aqueous sodium carbonate solution and the phases were separated. After two further extractions the combined organic extracts were washed with water and brine and dried over sodium sulfate. After filtration the compound was adsorbed onto silica gel and purified by flash column (10% ethyl acetate-iso-hexane) to yield 3,5-dichloropyridazine (5.6 g, 67%) as a pale yellow solid. A sample of 3,5-dichloropyridazine (0.43 g, 2.9 mmol) was dissolved in tetrahydrofuran (10 ml) under nitrogen and cooled to −65° C. 1,2-(Bis(diphenylphosphino)ethane)-dichloronickel(II) (0.08 g, 0.15 mmol) was added followed by 4-fluorophenylzinc bromide (11.6 ml of a 0.5 M solution in tetrahydrofuran). The mixture was warmed to −10° C. over 4 hours and poured onto a mixture of ethyl acetate/water (30 ml/10 ml). The phases were separated and the aqueous phase was extracted twice with ethyl acetate. The combined organic layers were washed with brine, dried over sodium sulfate and adsorbed onto silica gel. Purification by flask column chromatography (10% ethyl acetate-iso-hexane) gave the title compound (0.35 g, 58%) as a red solid.

Description 66:
4-Chloro-6-[4-trifluoromethylphenyl]pyrimidine

To a slurry of 4,6-dichloropyrimidine (2 g, 13.4 mmol), 4-trifluoromethylphenylboronic acid (3.06 g 16.1 mmol) and tripotassium phosphate (5.70 g 26.8 mmol) in 1,4-dioxan (20 ml) degassed with nitrogen for 10 minutes was added tetrakis (triphenylphosphine)palladium(0) (0.78 g, 0.67 mmol). The reaction mixture was then heated at 100° C. for 18 hours. The reaction mixture was diluted with ethyl acetate and filtered through a pad of Hyflo™. The filtrate was evaporated under reduced pressure to give an oil. The oil was taken up in ethyl acetate and washed with brine. The ethyl acetate extracts were then combined, dried ($MgSO_4$) filtered and evaporated under reduced pressure to give a dark red oil. The oil was purified by flash chromatography eluting with hexane (500 ml) hexane/ethyl acetate (10:1) as eluant. The appropriate fractions were combined and evaporated under reduced pressure to give a solid (2.1 g) as a mixture of desired product and 4,6-bis-[4-trifluoromethylphenyl]pyrimidine (9:1).

Description 67: 4,6-Dichloro-2-methylpyrimidine

A mixture of 4,6-dihydroxy-2-methylpyrimidine (15 g, 120 mmol) and phosphorus oxychloride (150 ml) were heated at reflux overnight. After allowing to cool the reaction mixture was concentrated to ~30 ml and then poured onto ice. The reaction mixture was extracted with ethyl acetate (3×75 ml). The organic extracts were combined, washed with base, brine, dried over magnesium sulfate, filtered and evaporated to give the title compound (13.4 g, 69%).

Description 68: 4-Chloro-2-methyl-6-[4-trifluoromethylphenyl]pyrimidine

Prepared from Description 67 and 4-trifluoromethylphenylboronic acid according to the procedure of Description 66.

Palladium-Catalysed Arylation Reactions of Amines.

Couplings of an amine and a heterocyclic halide were, unless otherwise stated, carried out according to one of the two general procedures below. The procedures have been routinely performed on scales of 0.5 mmol up to 10 mmol and representative procedures are described on a 1 mmol scale.

Description 69: First General Procedure for the Coupling of Amines with Heterocyclic Chlorides.

An amine (1.2 mmol), a heterocyclic halide (1.0 mmol), tris(dibenzylideneacetone)dipalladium(0) (23 mg, 0.025 mmol) and 2-(dicyclohexylphosphino)biphenyl (18 mg, 0.05 mmol) were added to a dry flask under a nitrogen atmosphere. Sodium t-butoxide (144 mg, 1.5 mmol) and para-xylene (3 ml) were introduced and the reaction mixture degassed by bubbling nitrogen through for 5 minutes. The reaction was heated at 100° C. with stirring for 15 hours, then cooled to room temperature. The reaction was partitioned between ethyl acetate (20 ml) and water (5 ml) and the aqueous phase extracted with more ethyl acetate (×2). The combined organic layers were washed with brine dried ($Na_2SO_4$) and evaporated The crude mixture was adsorbed onto silica gel, then purified by flash column chromatography. Where required, further purification was achieved by recrystallisation from alcoholic solvents.

Description 70: Second General Procedure for the Coupling of Amines with Heterocyclic Chlorides.

An amine (1.2 mmol), a heterocyclic halide (1.0 mmol) and sodium t-butoxide (144 mg, 1.5 mmol) were added to a dried flask under a nitrogen atmosphere. para-xylene or toluene (5 ml) was introduced and the reaction mixture degassed. 2'-(Dimethylamino)-2-biphenylyl palladium (II) chloride dinorbornylphosphine complex [see Angew. Chem., 2002, 41, 3668; CAS number 359803-53-5] (2 mol %) was added, the reaction was degassed once more, then heated to 100° C. (or 130° C. if required) for 18 hours. The reaction was loaded directly onto silica gel and purified by flash column chromatography. Where required, further purification was achieved by crystallisation or preparative hplc. In some cases, an alternative work-up procedure was to partition the crude reaction mixture between water and an organic solvent. The organic extract was then dried ($Na_2SO_4$), evaporated and purified as above.

Description 71: 5-Amino-1,3-dimethylquinolin-2(1H)-one

Prepared from 3-methyl-5-nitroquinoline (JOC, 1958, 23, 271) according to the procedures outlined in Descriptions 17, 18 and 20.

Description 72: N-(6-Chloropyrimidin-4-yl)isoquinolin-5-amine

A mixture of 4,6-dichloropyrimidine (5 g, 34 mmol), isoquinolin-5-amine (5.3 g, 37 mmol), 2'-(dimethylamino)-2-biphenylyl palladium (II) chloride dinorbornylphosphine complex. [see Angew. Chem., 2002, 41, 3668; CAS number 359803-53-5] (940 mg, 2 mmol) and sodium tert-butoxide (4.8 g, 50 mmol) in p-xylene (100 ml) was degassed thoroughly and heated under nitrogen at 100° C. for 16 hours. The cooled reaction mixture was purified by column chromatography over silica (eluant 1% MeOH in DCM) to give the title compound (1.5 g, 17%).

Description 73: 4-Chloro-5-methoxy-6-[4-trifluoromethylphenyl]pyrimidine

Prepared from 4,6-dichloro-5-methoxypyrimidine (Organic Process Research and Development, 1(4), 1997, 300-310) according to the procedure outlined in Description 66.

Description 74: 4-Chloro-5-methyl-6-[4-trifluoromethylphenyl]pyrimidine

Prepared from 4,6-dichloro-5-methylpyrimidine according to the procedure outlined in Description 66.

Description 75: 1-Benzothien-7-ylboronic acid

A solution of 7-bromo-1-benzothiophene (19.9 g, 0.094 mol) in absolute ether (200 ml) was treated with a 1.6 M solution of n-butyllithium in hexane (0.14 mol, 88 ml) at −78° C. The solution was stirred at −78° C. for 10 minutes then treated with trimethyl borate (15 ml, 0.14 mol). The mixture was allowed to warm to −10° C. then quenched with an excess of dilute hydrochloric acid. The organic layer was separated, dried, evaporated, and the residue was recrystallised from aqueous ethanol to yield the title compound (10 g, 60%).

Description 76: 1-Benzyl-4,4-diethoxypiperidine

A solution of 1-benzylpiperidin-4-one (240 ml, 1.3 mol) in ethanol (500 ml) was saturated with gaseous hydrogen chloride under cooling on an ice bath. The mixture was treated with tetraethoxysilane (300 ml), kept overnight at RT, then poured with stirring into a mixture of diethyl ether (500 ml), potassium carbonate (500 g) and water (1000 ml). The organic layer was separated, the diethyl ether was evaporated and the residue was distilled under vacuum to give the title compound (369 g, 77%).

Description 77: {2-[(4,4-Diethoxyipieridin-1-yl)methyl]phenyl}boronic Acid

To a solution of Description 76 (189 g, 0.72 mol) in anhydrous diethyl ether (920 ml), tetramethylethylenediamine (120 ml, 0.8 mol) and 1.6 M n-butyllithium solution in hexane (500 ml) were added. The mixture was stirred overnight at room temperature, cooled to −100° C., then treated with trimethyl borate (90 ml, 0.8 mol). The mixture was allowed to warm to RT, the diethyl ether was evaporated and a solution of phosphoric acid (18 ml, 0.267 mol) in water (100 ml) was added to the residue. The mixture was evaporated, diluted with hexane (1000 ml) and the precipitate was filtered. The filtrate was evaporated, the oil obtained was diluted with hexane (1000 ml), and the above procedure was repeated 2-3 times. The precipitates were combined and extracted with boiling DCM (5×500 ml). The solvent was evaporated and the oil obtained was refluxed with hexane. The precipitated solid was filtered and dried to give 72.4 g (32%) of a light brown powder. Recrystallisation from toluene gave the title compound (50 g, 22%).

Description 78: {2-[(4-Oxopiperidin-1-yl)methyl]phenyl}boronic Acid

To a suspension of Description 77 (10 g, 32.5 mmol) in water (20 ml), concentrated hydrochloric acid (7.5 ml) was added and the mixture then heated to 37-40° C. Almost complete dissolution of the precipitate was seen. The mixture was left for 2 hours at RT, filtered, neutralised with aqueous ammonia (7.5 ml) and then extracted with DCM (30 ml). The solvent was evaporated and the oil was dried azeotropically by addition of toluene then evaporation. The residue was then triturated with diethyl ether at reflux and collected by filtration to give the title compound (5.5 g, 73%).

Description 79: [3-(1H-Pyrazol-1-yl)phenyl]boronic acid

Prepared from 1-(3-bromophenyl)-1H-pyrazole according to the procedure of Description 75 to give the title compound (117 g, 85%).

Description 80: N-(6-Chloropyrimidin-4-yl)-6-fluoro-3-methylisoquinolin-5-amine

Prepared from Description 16 and 4,6-dichloropyrimidine according to Description 72.

Description 81: Third General Procedure for the Coupling of Amines with Heterocyclic Chlorides.

An amine (1.0 mmol), a heterocyclic halide (1.0 mmol), caesium carbonate (163 mg, 0.5 mmol), tris(dibenzylideneacetone)dipalladium(0) (18 mg, 0.02 mmol) and 4,5-bis(diphenylphosphino)-9,9-dimethylxanthene (34 mg, 0.06 mmol) were suspended in dioxane (5 ml). The mixture was degassed for 5 minutes by bubbling nitrogen through and then heated to reflux for 12 hours. After cooling to room temperature, the mixture was concentrated under reduced pressure, the residue was partitioned between ethyl acetate/water, and the aqueous phase was extracted with ethyl acetate. The combined organic phases were washed (brine), dried (sodium sulfate) and concentrated. The compounds were purified by flash chromatography (ethyl acetate/isohexanes). Where necessary, subsequent HPLC purification was performed.

Description 82: General Procedure for the Coupling of Boronic Acids with Heterocyclic Chlorides.

The appropriate boronic acid (0.2 mmol), Pd(dppf)$_2$Cl$_2$ (2 mg, 0.003 mmol), 2M Na$_2$CO$_3$ (100 µl), N-(6-chloropyrimidin-4-yl)isoquinolin-5-amine (Description 72, 25 mg, 0.1 mmol) and 1,4-dioxane (1 ml) were heated at 170° C. for 10 minutes in the microwave. Water (2 ml) and DCM (2 ml) was added to the reaction mixture, which was then placed on a Vortex for 20 sec and poured through a phase separation cartridge to collect the DCM layer. This layer was evaporated and the residue purified using mass directed HPLC.

Examples 1 to 4 were prepared using isoquinolin-5-amine and the indicated compounds using the procedure of Description 69.

EXAMPLE 1

N-(4-Phenylpyridin-2-yl)isoquinolin-5-amine

Prepared from Description 46 to give a colourless solid (0.07 g, 17%). m/z (ES$^+$) 298 (M+H$^+$).

EXAMPLE 2

N-{4-[4-Trifluoromethoxyphenyl]pyridin-2-yl}isoquinolin-5-amine

Prepared from Description 44 to give a colourless solid (0.085 g, 22%). m/z (ES$^+$) 382 (M+H$^+$).

EXAMPLE 3

N-{4-[3-Trifluoromethylphenyl]pyridin-2-yl}isoquinolin-5-amine

Prepared from Description 45 to give a colourless solid (0.105 g, 37%). m/z (ES$^+$) 366 (M+H$^+$).

EXAMPLE 4

N-{4-[4-Trifluoromethylphenyl]pyridin-2-yl}isoquinolin-5-amine

Prepared from Description 43 to give a lemon yellow solid (1.42 g, 54%). m/z (ES$^+$) 366 (M+H$^+$).

EXAMPLE 5

N-{5-[4-Trifluoromethylphenyl]pyridin-2-yl}isoquinolin-5-amine

To a mixture of 5-aminoisoquinoline (2.53 g, 17.5 mmol) and 2,5-dibromopyridine (3.62 g, 15.3 mmol) was added palladium acetate (0.17 g, 0.76 mmol) and rac-2,2'-bis(diphenylphosphino)-1,1'-binaphthyl (0.47 g, 0.76 mmol). The flask was flushed with nitrogen and p-xylene was added followed by sodium tert-butoxide (2.2 g, 22.9 mmol). Nitrogen was bubbled through the mixture for 5 minutes and the reaction was then heated with stirring at 130° C. for 12 hours under an atmosphere of nitrogen. The mixture was allowed to cool to room temperature and poured onto a mixture of chloroform/water (200 ml/20 ml). The phases were separated and the aqueous phase was extracted twice with chloroform. The combined organic layers were washed with brine, dried over sodium sulfate and adsorbed onto silica gel. Purification by flash chromatography (50% ethyl acetate-isohexane) followed by recrystallisation from ethanol gave N-(5-bromopyridin-2-yl)isoquinolin-5-amine (3.4 g, 74%). A portion (0.71 g, 2.37 mmol) was added to 4(trifluoromethyl) phenylboronic acid (0.68 g, 3.59 mmol) in anhydrous dioxane (10 ml) and tetrakis(triphenylphosphino)-palladium (0) (0.14 g, 0.12 mmol) and saturated aqueous sodium carbonate solution (4 ml) were added. Nitrogen was bubbled through the mixture for 5 minutes and the reaction was then heated with stirring at 100° C. for 12 hours under an atmosphere of nitrogen. The mixture was allowed to cool to room temperature and poured into a mixture of ethyl acetate/water (100 ml/30 ml). The phases were separated and the aqueous phase was extracted two times more with ethyl acetate. The combined organic layers were washed with brine, dried over sodium sulfate and adsorbed onto silica gel. Purification by flash chromatography (50% ethyl acetate-iso-hexane) followed by recrystallisation from methanol/water (1:1) yielded the title compound (0.22 g, 25%). m/z (ES$^+$) 366 (M+H$^+$).

EXAMPLE 6

5-({4-[4-Trifluoromethylphenyl]pyridin-2-2-yl}oxy)isoquinoline

To a mixture of Description 43 (0.22 g, 0.86 mmol) and 5-hydroxyisoquinoline (0.15 g, 1.0 mmol) in anhydrous N,N-dimethylacetamide (2.5 ml) was added sodium hydride (0.1 g, 2.5 mmol) in one portion under nitrogen. The mixture was heated with stirring at 150° C. for 15 hours under an atmosphere of nitrogen, allowed to cool to room temperature and poured into a mixture of chloroform/water (30 ml/10 ml). The phases were separated and the aqueous phase was extracted two times more with chloroform. The combined organic layers were washed with brine, dried over sodium sulfate and adsorbed onto silica gel. Purification by flash chromatography (50% ethyl acetate-iso-hexane) followed by recrystallisation from ethanol/water (1:1) gave the title compound (15 mg, 5%) as an off white solid.

m/z (ES$^+$) 367 (M+H$^+$).

Examples 7 to 10 were prepared using isoquinolin-5-amine and the indicated compound using the process of Description 69.

EXAMPLE 7

N-{6-Methyl-4-[4-trifluoromethylphenyl]pyridin-2-yl}isoquinolin-5-amine

Prepared from Description 51 to give a colourless solid (0.12 g, 23%). m/z (ES$^+$) 380 (M+H$^+$).

EXAMPLE 8

N-{6-Methoxy-4-[4-trifluoromethylphenyl]pyridin-2-yl}isoquinolin-5-amine

Prepared from Description 53 to give a colourless solid (0.15 g, 28%). m/z (ES$^+$) 396 (M+H$^+$).

EXAMPLE 9

N-{6-Chloro-4-[4-trifluoromethyl)phenyl]pyridin-2-yl}isoquinolin-5-amine

Prepared from Description 48 to give a yellow solid (0.14 g, 29%). m/z (ES$^+$) 400 (M+H$^+$).

EXAMPLE 10

N-{6-Chloro-4-(pyridin-4-yl)pyridin-2-yl}isoquinolin-5-amine

Prepared from Description 49 to give a colourless solid (0.08 g, 17%). m/z (ES$^+$) 333 (M+H$^+$).

Examples 11 to 16 were prepared from the indicated compounds using the process of Description 70.

EXAMPLE 11

3-Methyl-N-{4-[4-trifluoromethIlphenyl]pyridin-2-yl}isoquinolin-5-amine

Prepared from Description 43 and Description 2 as a light brown solid (75 mg, 26%). m/z (ES$^+$) 380 (M+H$^+$).

EXAMPLE 12

1-Methyl-N-{4-[4-trifluoromethylphenyl]pyridin-2-yl}isoquinolin-5-amine

Prepared from Description 43 and Description 4 as a yellow solid (63 mg, 21%). m/z (ES$^+$) 380 (M+H$^+$).

EXAMPLE 13

6,8-Difluoro-3-methyl-N-{4-[4-trifluoromethylphenyl]pyridin-2-yl}isoquinolin-5-amine Prepared from Description 43 and Description 10 as a white solid (69 mg, 19%). m/z (ES$^+$) 416 (M+H$^+$).

EXAMPLE 14

3-Methyl-7-trifluoromethyl-N-{4-[4-triflouromethylphenyl]pyridin-2-yl}isoquinolin-5-amine Prepared from Description 43 and Description 11 as a white solid (190 mg, 50%). m/z (ES$^+$) 448 (M+H$^+$).

EXAMPLE 15

8-Fluoro-3-methyl-N-{4-[4-trifluoromethylphenyl]pyridin-2-yl}isoquinolin-5-amine Prepared from Description 43 and Description 13 as an off white solid (120 mg, 35%). m/z (ES$^+$) 398 (M+H$^+$).

EXAMPLE 16

6-Fluoro-3-methyl-N-{4-[4-trifluoromethylphenyl]pyridin-2-yl}isoquinolin-5-amine Prepared from Description 43 and Description 16 as a white solid (130 mg, 38%). m/z (ES$^+$) 398 (M+H$^+$).

EXAMPLE 17

N-{4-[4-Trifluoromethylphenyl]pyridin-2-yl}quinolin-5-amine

Prepared from Description 43 and quinolin-5-amine to give a colourless solid (0.095 g, 26%).

m/z (ES$^+$) 366 (M+H$^+$).

EXAMPLE 18

3-Methyl-N-{4-[4-trifluoromethylphenyl]pyridin-2-yl}cinnolin-5-amine

Prepared from Description 43 and 3-methylcinnolin-5-amine to give a green solid (0.195 g, 37%). m/z (ES$^+$) 380 (M+H$^+$).

EXAMPLE 19

1-Methyl-5-({-4[4-trifluoromethylphenyl]pyridin-2-yl}amino)quinolin-2(1H-one

Prepared from Description 43 and Description 20 in 1:1 stoicheiometry according to the procedure of Description 70 as a light brown solid (20 mg, 18%). m/z (ES$^+$) 396 (M+H$^+$).

EXAMPLE 20

1-Methyl-5-({4-[4-trifluoromethylphenyl]pyridin-2-yl}amino)-3,4-dihydroquinolin-2(1H)-one Prepared from Description 43 and Description 19 in 1:1 stoicheiometry according to the procedure of Description 70 as a light brown solid (22 mg, 19%). m/z (ES$^+$) 398 (M+H$^+$).

EXAMPLE 21

1-Methyl-N-{4-[4-trifluoromethylphenyl]pyridin-2-yl}-1H-indazol-4-amine

Prepared from Description 43 and Description 22 according to the procedure of Description 69 to give a colourless solid (0.067 g, 28%). m/z (ES$^+$) 369 (M+H$^+$).

EXAMPLE 22

N-{4-[4-Trifluoromethylphenyl]pyridin-2-yl}-1H-indazol-4-amine

Reaction of Description 43 and Description 25 according to the procedure of Description 69 led to the SEM protected adduct (0.67 g, 52%). This compound (0.60 g, 1.24 mmol) was dissolved in ethanol (20 ml) and 6N HCl (5 ml) was added. The reaction mixture was heated at reflux for 18 hours. The solvent was evaporated under reduced pressure and the residue partitioned between ethyl acetate and saturated sodium carbonate solution. The ethyl acetate extracts were combined, washed with brine, dried over magnesium sulphate, filtered and evaporated under reduced pressure to give an oil. The oil was purified by flash chromatography using hexane/ethyl acetate (3:1) (500 ml) then hexane/ethyl acetate (1:1) as eluant to give an off white solid which was triturated with hexane and collected by filtration (120 mg, 27%). m/z (ES$^+$) 355 (M+H$^+$).

EXAMPLE 23

6-Fluoro-1-methyl-N-{4-[4-trifluoromethylphenyl]pyridin-2-yl}-1H-indazol-4-amine Prepared from Description 43 and Description 32 according to the procedure of Description 70 as a white solid (95 mg, 29%). m/z (ES$^+$) 387 (M+H$^+$).

EXAMPLE 24

1-Methyl-6-trifluoromethyl-N-{4-[4-trifluoromethylphenyl]pyridin-2-yl}-1H-indazol-4-amine Prepared from Description 43 and Description 33 according to the procedure of Description 70 as a white solid (104 mg, 28%). m/z (ES$^+$) 437 (M+H$^+$).

EXAMPLE 25

N-{5-[4-Trifluoromethylphenyl]pyridazin-3-1}isoquinolin-5-amine

Prepared from Description 54 and isoquinolin-5-amine according to the procedure of Description 69 to give an orange solid (0.44 g, 42%). m/z (ES$^+$) 367 (M+H$^+$).

EXAMPLE 26

N-(5-[3-Cyanophenyl]pyridazin-3-yl)isoquinolin-5-amine

Prepared from Description 58 and Description 69 to give a light brown solid (0.11 g, 30%).
m/z (ES$^+$) 324 (M+H$^+$).

Examples 27 to 29 were preparped from isoquinolin-5-amine and the indicated compound using the process of Description 70.

EXAMPLE 27

N-[5-(4-Methoxyphenyl)pyridazin-3-yl]isoquinolin-5-amine

Prepared from Description 62 as an off white solid (37 mg, 11%). m/z (ES$^+$) 329 (M+H$^+$).

EXAMPLE 28

N-[5-(4-tert-Butylphenyl)pyridazin-3-yl]isoquinolin-5-amine

Prepared from Description 56 as an off white solid (233 mg, 34%). m/z (ES$^+$) 355 (M+H$^+$).

EXAMPLE 29

N-{5-[2-Fluoro-4-trifluoromethylphenyl]pyridazin-3-yl}isoquinolin-5-amine

Prepared from Description 64 as an off white solid (120 mg, 21%). m/z (ES$^+$) 385 (M+H$^+$).

EXAMPLE 30

N-{6-Chloro-5-[4-trifluoromethylphenyl]pyridazin-3-yl}isoquinolin-5-amine

Prepared from Description 59 and isoquinolin-5-amine according to the procedure of Description 69 to give a brown solid (0.66 g, 23%). m/z (ES$^+$) 401 (M+H$^+$).

EXAMPLE 31

N-[5-(3-Methylpyridin-2-yl)pyridazin-3-yl]isoquinolin-5-amine

Prepared from Description 60 and isoquinolin-5-amine according to the procedure of Description 70 as a light green solid (88 mg, 32%). m/z (ES$^+$) 314 (M+H$^+$).

EXAMPLE 32

N-{4,5-bis[4-Trifluoromethylphenyl]pyridazin-3-yl}isoquinolin-5-amine

To a mixture of Example 30 (0.08 g, 0.2 mmol) and 4-trifluoromethylphenylboronic acid (0.057 g, 0.3 mmol) in anhydrous dioxane (2 ml) was added (1,1'-bis(diphenylphosphino)ferrocene)dichloropalladium (0.007 g, 0.009 mmol) and saturated aqueous sodium carbonate solution (0.3 ml). The mixture was irradiated in a microwave reactor at 170° C. for 10 minutes, allowed to cool to room temperature and poured onto a mixture of chloroform/water (30 ml/10 ml). The phases were separated and the aqueous phase was extracted two times more with chloroform. The combined organic layers were washed with brine, dried over sodium sulfate and adsorbed onto silica gel. Purification by flash column chromatography (ethyl acetate) yielded the title compound (35 mg, 34%) as a yellow solid. m/z (ES$^+$) 511 (M+H$^+$).

EXAMPLE 33

3-Methyl-N-{5-[4-trifluoromethylphenyl]pyridazin-3-yl}isoquinolin-5-amine

Prepared from Description 54 and Description 2 according to the procedure of Description 70 as a yellow solid (6 mg, 2%). m/z (ES$^+$) 381 (M+H$^+$).

EXAMPLE 34

1-Methyl-N-1-{5-[4-trifluoromethylphenyl]pyridazin-3-yl}isoquinolin-5-amine

Prepared from Description 54 and Description 4 according to the procedure of Description 70 as a light brown solid (20 mg, 2%). m/z (ES$^+$) 381 (M+H$^+$).

EXAMPLE 35

N-{5-[4-Trifluoromethylphenyl]pyridazin-3-yl}-5,6,7,8-tetrahydroisoquinolin-5-amine To a solution of Description 59 (786 mg, 2.68 mmol) in anhydrous dimethylacetamide (2 ml) was added Description 5 (397 mg, 2.68 mmol). The reaction mixture was heated at 100° C. for 24 hours then cooled and partitioned between ethyl acetate (15 ml) and water (15 ml). The aqueous layer was extracted with more ethyl acetate (15 ml) and the combined organic phases washed with water (2×20 ml), then dried (MgSO$_4$), filtered and evaporated to give a brown oil. Purification by flash column chromatography on silica using 6% methanol in dichloromethane as the eluant gave a brown oil (450 mg, 42%). This oil (450 mg, 1.1 mmol) was dissolved in methanol (10 ml) and 10% palladium on carbon (100 mg), and ammonium formate (700 mg, 11 mmol, 10 eq) were added and the reaction heated at 50° C. for 90 minutes. The reaction was cooled, then filtered and the solvent evaporated. The resulting solid was extracted into ethyl acetate (2×30 ml) and washed with water (2×30 ml), the organic layer was then dried over MgSO$_4$, filtered and evaporated. The resulting brown oil was purified by column chromatography on silica eluting with 3% methanol in dichloromethane with 0.5% ammonia to give the title compound as a white solid (31 mg, 8%). m/z (ES$^+$) 371 (M+H$^+$). Examples 36 to 41 were prepared using the indicated compounds using the process of Description 70.

EXAMPLE 36

6,8-Difluoro-3-methyl-N-{5-[4-trifluoromethylphenyl]pyridazin-3-yl}isoquinolin-5-amine Prepared from Description 54 and Description 10 as an off white solid (34 mg, 9%). m/z (ES$^+$) 417 (M+H$^+$).

EXAMPLE 37

3-Methyl-7-trifluoromethyl-N-{5-[4-trifluoromethylphenyl]pyridazin-3-yl}isoquinolin-5-amine Prepared from Description 54 and Description 11 as an off white solid (63 mg, 16%). m/z (ES$^+$) 449 (M+H$^+$).

EXAMPLE 38

8-Fluoro-3-methyl-N-{5-[4-trifluoromethylphenyl]pyridazin-3-yl}isoquinolin-5-amine Prepared from Description 54 and Description 13 as an off white solid (26 mg, 7%). m/z (ES$^+$) 399 (M+H$^+$).

EXAMPLE 39

6-Fluoro-3-methyl-N-{5-[4-trifluoromethylphenyl]pyridazin-3-}isoquinolin-5-amine Prepared from Description 54 and Description 16 as an off white solid (56 mg, 16%). m/z (ES$^+$) 399 (M+H$^+$).

EXAMPLE 40

3-Methyl-N-{5-[4-trifluoromethylphenyl]pyridazin-3-yl}cinnolin-5-amine

Prepared from Description 54 and 3-methylcinnolin-5-amine as a yellow solid (75 mg, 23%).
m/z (ES$^+$) 382 (M+H$^+$).

EXAMPLE 41

1-Methyl-5-({5-[4-trifluoromethylphenyl]pyridazin-3-yl}amino)quinolin-2(1H)-one

Prepared from Description 54 and Description 20 in 1:1 stoicheiometry as a light brown solid (35 mg, 36%). m/z (ES$^+$) 397 (M+H$^+$).

EXAMPLE 42

1-Methyl-N-{5-[4-trifluoromethylphenyl]pyridazin-3-yl}-1H-indazol-4-amine

Prepared from Description 54 and Description 22 according to the procedure of Description 69 as a yellow solid (16 mg, 3%). m/z (ES$^+$) 370 (M+H$^+$).

EXAMPLE 43

2-Methyl-N-{5-[4-trifluoromethylphenyl]pyridazin-3-yl}-2H-indazol-4-amine

Prepared from Description 54 and Description 23 according to the procedure of Description 70 as an off white solid (10 mg, 11%). m/z (ES$^+$) 370 (M+H$^+$).

EXAMPLE 44

N-{5-[4-Trifluoromethylphenyl]pyridazin-3-yl}-1H-indazol-4-amine

Reaction of Description 59 and Description 25 according to the procedure of Description 70 gave the coupled product (595 mg, 1.1 mmol) which was dissolved in methanol (5 ml). 10% 30, Palladium on carbon (100 mg) and ammonium formate (693 mg, 11 mmol, 10 eq) were added and the reaction heated at 50° C. for 3 hours. The reaction was cooled, then filtered and the solvent evaporated. The resulting solid was partitioned between ethyl acetate (30 ml) and water (30 ml) and the aqueous phase extracted with ethyl acetate (30 ml). The combined organic phases were washed with water (2×30 ml), then dried over $MgSO_4$ and evaporated to give the dechlorinated compound (568 mg, quantitative). This compound (475 mg, 0.98 mmol) was dissolved in ethanol (20 ml), hydrochloric acid (5N, 6 ml) was added and the solution heated at 80° C. for 30 minutes. The reaction was cooled, the solvent evaporated and the residue partitioned between ethyl acetate (50 ml) and water (30 ml). The aqueous phase was extracted with ethyl acetate (30 ml) and the combined organic phases were washed with saturated aqueous sodium carbonate (50 ml), brine (50 ml) and water (50 ml), then dried over $MgSO_4$ and evaporated. The yellow oil was purified by flash column chromatography on silica eluting with 75% ethyl acetate in dichloromethane, and the resulting solid triturated with diethyl ether and hexane to give the title compound as a yellow solid (148 mg, 43%). m/z ($ES^+$) 356 ($M+H^+$).

Examples 45 to 50 were prepared from the indicated compounds using the process of Description 70.

EXAMPLE 45

6-Fluoro-1-methyl-N-{5-[4-trifluoromethylphenyl] pyridazin-3-yl}-1H-indazol-4-amine Prepared from Description 54 and Description 32 as a white solid (80 mg, 24%). m/z ($ES^+$) 388 ($M+H^+$).

EXAMPLE 46

1-Methyl-6-trifluoromethyl-N-{5-[4-trifluoromethylphenyl]pyridazin-3-yl}-1H-indazol-4-amine Prepared from Description 54 and Description 33 as a white solid (24 mg, 6%). m/z ($ES^+$) 438 ($M+H^+$).

EXAMPLE 47

N-{5-[4-Trifluoromethylphenyl]pyridazin-3-yl}imidazor[1,5-a]pyridin-8-amine

Prepared from Description 54 and Description 39 as an off white solid (80 mg, 10%). m/z ($ES^+$) 356 ($M+H^+$).

EXAMPLE 48

N-{5-[4-Trifluoromethylphenyl]pyridazin-3-yl}imidazo[1,2-a]pyridin-5-amine

Prepared from Description 54 and imidazo[1,2-a]pyridin-5-amine (*Medicinal Chemistry Research*, 1997, 7(8), 436464) as an off white solid (120 mg, 15%). m/z ($ES^+$) 356 ($M+H^+$).

EXAMPLE 49

N-{5-[4-Trifluoromethylphenyl]pyridazin-3-yl}[1,2,3]triazolo[1,5-a]pyridin-4-amine Prepared from Description 54 and Description 42 as an orange solid (22 mg, 4%). m/z ($ES^+$) 329 ($M+H^+$).

EXAMPLE 50

2-Methyl-N-{5-[4-trifluomethylphenyl]pyridazin-3-yl}-1,3-benzothiazol-6-amine

Prepared from Description 54 and 6-amino-2-methylbenzothiazole as a yellow solid (120 mg, 25%). m/z ($ES^+$) 387 ($M+H^+$).

EXAMPLE 51

N-{6-(4-Fluorophenyl)pyridazin-4-yl}isoquinolin-5-amine

Prepared from Description 65 and isoquinolin-5-amine according to the procedure of Description 69 as a colourless solid (35 mg, 31%). m/z ($ES^+$) 317 ($M+H^+$).

EXAMPLE 52

N-{6-[4-Trifluoromethylphenyl]pyrimidin-4-yl}isoquinolin-5-amine

Prepared from Description 66 and isoquinolin-5-amine according to the procedure of Description 69 as an off white solid (50 mg, 7%). m/z ($ES^+$) 367 ($M+H^+$).

Examples 53 to 61 were prepared from the indicated compounds using the process of Description 70.

EXAMPLE 53

3-Methyl-N-{6-[4-trifluoromethylphenyl]pyrimidin-4-yl}isoquinolin-5-amine

Prepared from Description 66 and Description 2 as a pink solid (16 mg, 5.4%). m/z ($ES^+$) 381 ($M+H^+$).

EXAMPLE 54

1-Methyl-N-{6-[4-trifluoromethylphenyl]pyrimidin-4yl}isoquinolin-5-amine

Prepared from Description 66 and Description 4 as an off white solid (13 mg, 4.4%). m/z ($ES^+$) 381 ($M+H^+$).

EXAMPLE 55

N-{6-[4-Trifluoromethylphenyl]pyrimidin-4-yl}-5,6,7,8-tetrahydroisoquinolin-5-amine Prepared from Description 66 and Description 5 as an off white solid (6 mg, 1%). m/z ($ES^+$) 371 ($M+H^+$).

EXAMPLE 56

6,8-Difluoro-3-methyl-N-{6-[4-trifluoromethylphenyl]pyrimidin-4-yl}isoquinolin-5-anine Prepared from Description 66 and Description 10 as an off white solid (130 mg, 37%). m/z ($ES^+$) 417 ($M+H^+$).

EXAMPLE 57

3-Methyl-7-trifluoromethyl-N-{6-[4-trifluoromethylphenyl]pyrimidin-4-yl}isoquinolin-5-amine Prepared from Description 66 and Description 11 as an off white solid (154 mg, 40%). m/z ($ES^+$) 449 ($M+H^+$).

EXAMPLE 58

8-Fluoro-3-methyl-N-{6-[4-trifluoromethylphenyl]
pyrimidin-4-yl}isoquinolin-5-amine Prepared from Description 66 and Description 13 as an off white solid (83 mg, 24%). m/z (ES$^+$) 399 (M+H$^+$).

EXAMPLE 59

6-Fluoro-3-methyl-N-{6-[4-trifluoromethylphenyl]
pyrimidin-4-yl}isoquinolin-5-amine Prepared from Description 66 and Description 16 as an off white solid (65 mg, 19%). m/z (ES$^+$) 399 (M+H$^+$).

EXAMPLE 60

3-Methyl-N-{2-methyl-6-[4-trifluoromethylphenyl]
pyrimidin-4-4}isoquinolin-5-amine Prepared from Description 68 and Description 2 as an off white solid (35 mg, 4%). m/z (ES$^+$) 395 (M+H$^+$).

EXAMPLE 61

3-Methyl-N-{6-[4-trifluoromethylphenyl]pyrimidin-4-yl}cinnolin-5-amine

Prepared from Description 66 and 3-methylcinnolin-5-amine as a yellow solid (36 mg, 11%).
m/z (ES$^+$) 382 (M+H$^+$).

EXAMPLE 62

1-Methyl-N-{6-[4-trifluoromethylphenyl]pyrimidin-4-yl}-1H-indazol-4-amine

Prepared from Description 66 and Description 22 according to the procedure of Description 69 as a yellow solid (17 mg, 3%). m/z (ES$^+$) 370 (M+H$^+$).

EXAMPLE 63

N-{6-[4-Trifluoromethylphenyl]pyrimidin-4-yl}-1H-indazol-4-amine

Prepared from Description 66 and Description 25 according to the procedure of Example 44 as a yellow solid (20 mg, 10%). m/z (ES$^+$) 356 (M+H$^+$). Examples 64 to 66 were made from the indicated compounds using the process of Description 70.

EXAMPLE 64

6-Fluoro-1-methyl-N-{6-[4-trifluoromethylphenyl]
pyrimidin-4-yl}-1H-indazol-4-amine Prepared from Description 66 and Description 32 as an off white solid (17 mg, 5%). m/z (ES$^+$) 388 (M+H$^+$).

EXAMPLE 65

1-Methyl-6-trifluoromethyl-N-{6-[4-trifluoromethylphenoyl]pyrimidin-4-yl}-1H-indazol-4-amine Prepared from Description 66 and Description 33 as a white solid (53 mg, 14%). m/z (ES$^+$) 438 (M+H$^+$).

EXAMPLE 66

N-{6-[4-Trifluoromethylphenyl]pyrimidin-4-yl}[1,2,3]triazolo[1,5-a]pyridin-4-amine Prepared from Description 66 and Description 42 as a yellow solid (15 mg, 3%). m/z (ES$^+$) 329 (M+H$^+$).

Examples 67 to 69 were prepared from the indicated compounds using the process of Description 81.

EXAMPLE 67

1,3-Dimethyl-5-({6-[4-trifluoromethylphenylphenyl]
pyrimidin-4-yl}amino)quinolin-2(1H)-one Prepared from Description 66 and Description 71. m/z (ES$^+$) 411 (M+H$^+$).

EXAMPLE 68

1,3-Dimethyl-5-({5-[4-trifluoromethylphenyl]pyridazin-3-yl}amino)quinolin-2(1H)-one Prepared from Description 54 and Description 71. m/z (ES$^+$) 411 (M+H$^+$).

EXAMPLE 69

1,3-Dimethyl-5-({4-[4-trifluoromethylphenyl]pyridin-2-yl}amino)quinolin-2(1H)-one Prepared from Description 43 and Description 71. m/z (ES$^+$) 410 (M+H$^+$).

EXAMPLE 70

N-{5-Methoxy-6-[4-trifluoromethylphenyl]pyrimidin-4-yl}isoquinolin-5-amine

Prepared from Description 73 according to the procedure of Description 70. m/z (ES$^+$) 412 (M+H$^+$).

EXAMPLE 71

N-{5-Methyl-6-[4-trifluoromethylphenyl]pyrimidin-4-yl}isoquinolin-5-amine

Prepared from Description 74 according to the procedure of Description 70. m/z (ES$^+$) 396 (M+H$^+$).

Examples 72 to 107 were prepared from the Description 72 and the indicated compound using the process of Description 82.

EXAMPLE 72

N-{6-[2,4-bis(Trifluoromethyl)phenyl]pyrimidin-4-yl}isoquinolin-5-amine

Prepared from [2,4-bis(trifluoromethyl)phenyl]boronic acid. m/z (ES$^+$) 434 (M+H$^+$).

EXAMPLE 73

N-[6-(1H-Indol-5-yl)pyrimidin-4-yl]isoquinolin-5-amine

Prepared from 1-H-indol-5-ylboronic acid. m/z (ES$^+$) 337 (M+H$^+$).

EXAMPLE 74

N-[6-(1-Benzothien-7-yl)pyrimidin-4-yl]isoquinolin-5-amine

Prepared from Description 75. m/z (ES+) 354 (M+H+).

EXAMPLE 75

1-{2-[6-(Isoquinolin-5ylamino)pyrimidin-4-yl]benzyl}piperidin-4-one

Prepared from Description 78. m/z (ES+) 409 (M+H+).

EXAMPLE 76

3-[6-(Isoquinolin-5-ylamino)pyrimidin-4-yl]benzaldehyde

Prepared from (3-formylphenyl)boronic acid. m/z (ES+) 326 (M+H+).

EXAMPLE 77

N-[6-(4-Ethylphenyl)pyrimidin-4-yl]isoquinolin-5-amine

Prepared from (4-ethylphenyl)boronic acid. m/z (ES+) 326 (M+H+).

EXAMPLE 78

N-{6-[3-(1H-Pyrazol-1-yl)phenyl]pyrimidin-4-yl}isoquinolin-5-amine

Prepared from Description 79. m/z (ES+) 364 (M+H+).

EXAMPLE 79

N-[6-(3-Fluorophenyl)pyrimidin-4-yl]isoquinolin-5-amine

Prepared from (3-fluorophenyl)boronic acid. m/z (ES+) 316 (M+H+).

EXAMPLE 80

N-{6-[4-Dimethylaminophenyl]pyrimidin-4-yl}isoquinolin-5-amine

Prepared from [4-dimethylaminophenyl]boronic acid. m/z (ES+) 341 (M+H+).

EXAMPLE 81

N-(6-Quinolin-8-ylpyrimidin-4-yl)isoquinolin-5-amine

Prepared from quinolin-8-ylboronic acid. m/z (ES+) 349 (M+H+).

EXAMPLE 82

N-[6-(3,5-Dichlorophenyl)pyrimidin-4-yl]isoquinolin-5-amine

Prepared from (3,5-dichlorophenyl)boronic acid. m/z (ES+) 366 (M+H+).

EXAMPLE 83

N-{6-[4-Benzyloxyvhenyl]pyrimidin-4-yl}isoquinolin-5-amine

Prepared from [4-benzyloxyphenyl]boronic acid. m/z (ES+) 404 (M+H+).

EXAMPLE 84

N-{6-[4-Trifluoromethoxyphenyl]pyrimidin-4-yl}isoquinolin-5-amine

Prepared from [4-trifluoromethoxyphenyl]boronic acid. m/z (ES+) 382 (M+H+).

EXAMPLE 85

N-{6-[3,5-bis(Trifluoromethyl)phenyl]pyrimidin-4-}isoquinolin-5-amine

Prepared from [3,5-bis(trifluoromethyl)phenyl]boronic acid. m/z (ES+) 434 (M+H+).

EXAMPLE 86

N-[6-(1-Naphthyl)pyrimidin-4-yl]isoquinolin-5-amine

Prepared from 1-naphthylboronic acid. m/z (ES+) 348 (M+H+).

EXAMPLE 87

N-[6-(4-tert-Butylphenyl)pyrimidinyl-4-yl]isoquinolin-5-amine

Prepared from (4-tert-butylphenyl)boronic acid. m/z (ES+) 354 (M+H+).

EXAMPLE 88

1-{4-[6-(Isoquinolin-5ylamino)pyrimidin-4-yl]phenyl}ethanone

Prepared from (4-acetylphenyl)boronic acid. m/z (ES+) 340 (M+H+).

EXAMPLE 89

4-[6-(Isoquinolin-5-ylamino)pyrimidinyl-4-yl]benzonitrile

Prepared from (4-cyanophenyl)boronic acid. m/z (ES+) 323 (M+H+).

EXAMPLE 90

3-[6-(Isoquinolin-5-ylamino)pyrimidin-4-yl]benzoic Acid

Prepared from 3-(dihydroxyboryl)benzoic acid. m/z (ES+) 342 (M+H+).

EXAMPLE 91

N-{6-[3-Trifluoromethylphenyl]pyrimidin-4-yl}isoquinolin-5-amine

Prepared from [3-(trifluoromethyl)phenyl]boronic acid. m/z (ES$^+$) 366 (M+H$^+$).

EXAMPLE 92

N-[6-(3-Methylphenyl)pyrimidin-4-yl]isoquinolin-5-amine

Prepared from (3-methylphenyl)boronic acid. m/z (ES$^+$) 312 (M+H$^+$).

EXAMPLE 93

N-(6-Mesitylpyrimidin-4-yl)isoquinolin-5-amine

Prepared from mesitylboronic acid. m/z (ES$^+$) 340 (M+H$^+$).

EXAMPLE 94

N-[6-(2-Fluoro-3-3-pyrimidin-3-ylphenyl)pyrimidin-4-yl]isoquinolin-5-amine

Prepared from (2-fluoro-3-pyridin-3-ylphenyl)boronic acid (WO-A-2002074772). m/z (ES$^+$) 393 (M+H$^+$).

EXAMPLE 95

N-{6-[4-Methylsulfonylphenyl]pyrimidin-4-yl}isoquinolin-5-amine

Prepared from [4-methylsulfonylphenyl]boronic acid. m/z (ES$^+$) 376 (M+H$^+$).

EXAMPLE 96

N-[6-(2-Naphthyl)pyrimidin-4-yl]isoquinolin-5-amine

Prepared from 2-naphthylboronic acid. m/z (ES$^+$) 348 (M+H$^+$).

EXAMPLE 97

N-[6-(4-Ethoxyphenyl)pyrimidin-4-]isoquinolin-5-amine

Prepared from (4-ethoxyphenyl)boronic acid. m/z (ES$^+$) 342 (M+H$^+$).

EXAMPLE 98

N-[6-(3-Nitrophenyl)pyrimidin-4-yl]isoquinolin-5-amine

Prepared from (3-nitrophenyl)boronic acid. m/z (ES$^+$) 343 (M+H$^+$).

EXAMPLE 99

N-[6-(4-Chlorophenyl)pyrimidin-4-yl]isoquinolin-5-amine

Prepared from (4-chlorophenyl)boronic acid. m/z (ES$^+$) 332 (M+H$^+$).

EXAMPLE 100

N-(6-Biphenyl-4-ylpyrimidin-4-yl)isoquinolin-5-amine

Prepared from biphenyl-4-ylboronic acid. m/z (ES$^+$) 374 (M+H$^+$).

EXAMPLE 101

N-[6-(1,3-Benzodioxol-5-yl)pyrimidin-4-yl]isoquinolin-5-amine

Prepared from 1,3-benzodioxol-5-ylboronic acid. m/z (ES$^+$) 342 (M+H$^+$).

EXAMPLE 102

N-[6-(3-Isopropylphenyl)pyrimidin-4-yl]isoquinolin-5-amine

Prepared from (3-isopropylphenyl)boronic acid. m/z (ES$^+$) 340 (M+H$^+$).

EXAMPLE 103

N-{6-[4-Methylthiohenyl]pyrimidin-4-yl}isoquinolin-5-amine

Prepared from [3-methylthiophenyl]boronic acid. m/z (ES$^+$) 344 (M+H$^+$).

EXAMPLE 104

N-[6-(2,5-Difluorophenyl)pyrimidin-4-yl]isoquinolin-5-amine

Prepared from (2,5-difluorophenyl)boronic acid. m/z (ES$^+$) 334 (M+H$^+$).

EXAMPLE 105

4-[6-(Isoquinolin-5-ylamino)pyrimidin-4-yl]phenol

Prepared from (4-hydroxyphenyl)boronic acid. m/z (ES$^+$) 314 (M+H$^+$).

EXAMPLE 106

N-[6-(4-Methoxyphenyl)pyrimidin-4-yl]isoquinolin-5-amine

Prepared from (4-methoxyphenyl)boronic acid. m/z (ES$^+$) 329 (M+H$^+$).

EXAMPLE 107

N-(6-Phenylpyrimidin-4-yl)isoquinolin-5-amine

Prepared from benzene boronic acid. m/z (ES$^+$) 299 (M+H$^+$).

EXAMPLE 108

6-Fluoro-3-methyl-N-{2-methyl-6-[4-trifluoromethylphenyl]pyrimidin-4-yl}isoquinolin-5-amine Prepared from Description 16 and Description 68 according to the procedure of Description 70 (0.21 g, 23%). m/z (ES$^+$) 413 (M+H$^+$).

EXAMPLE 109

N-[6-(4+Chlorophenyl)pyrimidin-4-yl]-6-fluoro-3-methylisoquinolin-5-amine

Prepared from Description 80 and (4-chlorophenyl)boronic acid according to Description 82 (42 mg, 42%). m/z (ES$^+$) 365 (M+H$^+$).

EXAMPLE 110

6-Fluoro-3-methyl-N-{6-[4-trifluoromethoxhenyl]pyrimidin-4-yl}isoquinolin-5-amine Prepared from Description 80 and [4-trifluoromethoxyphenyl]boronic acid according to Description 82 (57 mg, 50%). m/z (ES$^+$) 415 (M+H$^+$).

The above exemplified compounds of the present invention have been tested in the following assay and generally possess an IC$_{50}$<1 µM and, in the majority of cases, <200 µM.

Biological Methodology

Determination of in Vitro Activity

CHO cells, stably expressing recombinant human VR1 receptors and plated into black-sided 384-well plates, were washed twice with assay buffer (Hepes-buffered saline) and then incubated with 1 uM Fluo-3-AM for 60 minutes in darkness. Cells were washed twice more to remove excess dye, before being placed, along with plates containing capsaicin and test compounds in a Molecular Devices FLIPR The FLIPR simultaneously performed automated pharmacological additions and recorded fluorescence emmission from Fluo-3. In all experiments, basal fluorescence was recorded, before addition of test compounds and subsequent addition of a previously determined concentration of capsaicin that evoked 80% of the maximum respsonse. Inhibition of capsaicin evoked increases in intracellular [Ca$^{2+}$] were expressed relative to wells on the same plate to which capcaicin was added in the absence of test compounds. Increases in intracellular [Ca$^{2+}$] occuring after addition of test compound alone, prior to addition of capsaicin, allow determination of intrinsic agonist or partial agonist activity, if present.

Determination of in Vivo Efficacy in a Capsaicin Paw Flinch Model (Method adapted from Taniguchi et al, 1997, Br J Pharmacol. 122(5):809-12)

To determine in vivo functional occupancy of VR1 receptors, compounds are administered orally to male Sprague Dawley rats typically 1 hour prior to receiving an intraplantar injection of capsaicin (2 Tg dissolved in ethanol) and the number of flinches of the injected paw is recorded for 5 minutes immediately thereafter. Statistical analysis is performed using one-way ANOVA followed by Dunneft's test; p values <0.05 compared to capsaicin/vehicle-treated rats are considered significant.

Determination of in Vivo Efficacy in a Model of Inflammatory Pain (Method adapted from Hargreaves et al, 1988 Pain, 32(1):77-88).

Antinociceptive activity is determined using a rat carrageenan-induced thermal hyperalgesia assay. Inflammatory hyperalgesia is induced by intraplantar injection of carrageenan (lambda-carrageenan 0.1 ml of 1% solution made up in saline) into one hind paw. Compounds are given orally typically 2 hours after carrageenan and paw withdrawal latencies determined 1 hour later. Paw withdrawal latencies to application of noxious thermal stimuli to plantar surface of the hind paw are measured using the Hargreaves apparatus. Thermal hyperalgesia is defined as the difference in paw withdrawal latencies for saline/vehicle- and carrageenan/vehicle-treated rats. Paw withdrawal latencies for drug treated rats are expressed as a percentage of this response. Statistical analysis is performed using one-way ANOVA followed by Dunnett's test; p values <0.05 compared to carrageenan/vehicle-treated rats are considered significant.

The invention claimed is:
1. A compound of formula (I):

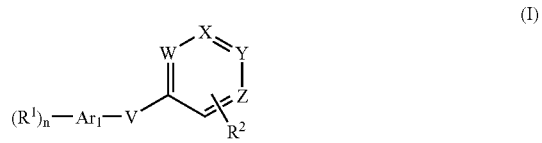

wherein
V represents NR$^5$, O, S, SO or S(O)$_2$;
W and X each independently represent CH or N;
Y represents N, CH or C—Ar$_2$, with the proviso that at least one, but no more than two, of W, X and Y are N;
Z represents CH or C—Ar$_2$, with the proviso that when Y is N or CH then Z is C—Ar$_2$, and with the further proviso that when Y is C—Ar$_2$ then Z is CH;
Ar$_1$ represents a fused 9 or 10 membered heterobicyclic ring system containing one, two, three or four heteroatoms selected from nitrogen, oxygen and sulfur, wherein at least one of the rings in said ring system is aromatic;
Ar$_2$ represents an aromatic ring selected from phenyl, pyridyl, pyridazinyl, pyrimidinyl and pyrazinyl; which aromatic ring is optionally fused to a phenyl ring, a five-membered heteroaromatic ring containing 1, 2, 3 or 4 heteroatoms selected from O, N and S at most 1 heteroatom being O or S, or a six-membered heteroaromatic ring containing 1, 2 or 3 N atoms; which aromatic ring is unsubstituted or substituted by one, two or three groups selected from halogen, hydroxy, C$_{1-6}$alkyl, C$_{2-6}$alkenyl, C$_{2-6}$alkynyl, phenylC$_{1-2}$alkoxy, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{3-5}$cycloalkylC$_{1-4}$alkyl, cyano, nitro, SR$^6$, SOR$^6$, SO$_2$R$^6$, COR$^6$, NR$^3$COR$^6$, CONR$^3$R$^4$, NR$^3$SO$_2$R$^6$, SO$_2$NR$^3$R$^4$, —(CH$_2$)$_m$carboxy, esterified —(CH$_2$)$_m$carboxy, —(CH$_2$)$_m$NR$^3$R$^4$, phenyl, naphthyl, a five-membered heteroaromatic ring containing 1,2, 3 or 4 heteroatoms selected from O, N and S at most 1 heteroatom being O or S and a six-membered heteroaromatic ring containing 1, 2 or 3 N atoms; where two C$_{1-6}$alkoxy groups are on adjacent atoms they may, together with the atoms to which they are attached, form a 5- or 6-membered partially saturated ring;
R$^1$ represents halogen, hydroxy, oxo, C$_{1-6}$alkyl, C$_{2-6}$alkenyl, C$_{2-6}$alkynyl, haloC$_{1-6}$alkyl, hydroxyC$_{1-6}$alkyl, C$_{1-6}$alkoxy, haloC$_{1-6}$alkoxy, hydroxyC$_{1-6}$alkoxy, C$_{3-7}$cycloalkyl, C$_{3-7}$cycloalkoxy, C$_{3-5}$cycloalkylC$_{1-4}$alkyl, cyano, nitro, SR$^6$, SOR$^6$, SO$_2$R$^6$, COR$^6$, NR$^3$COR$^6$, CONR$^3$R$^4$, NR$^3$SO$_2$R$^6$, SO$_2$NR$^3$R$^4$, —(CH$_2$)$_m$carboxy, esterified —(CH$_2$)$_m$carboxy or —(CH$_2$)$_m$NR$^3$R$^4$;

R² represents hydrogen, halogen, hydroxy, $C_{1-6}$alkyl, halo$C_{1-6}$alkyl, $C_{3-7}$cycloalkyl, $C_{1-6}$alkoxy, halo$C_{1-6}$alkoxy, unsubstituted phenyl or phenyl substituted with one or two groups selected from halogen, $C_{1-6}$alkyl, halo$C_{1-6}$alkyl, $C_{3-7}$cycloalkyl, $C_{1-6}$alkoxy or halo$C_{1-6}$alkoxy;

R³ and R⁴ are each independently hydrogen, $C_{1-6}$alkyl, $C_{2-6}$alkenyl, $C_{2-6}$alkynyl, $C_{3-7}$cycloalkyl or fluoro$C_{1-6}$alkyl;

or R³ and R⁴ and the nitrogen atom to which they are attached together form a heteroaliphatic ring of 4 to 7 ring atoms, optionally substituted by one or two groups selected from hydroxy or $C_{1-4}$alkoxy, which ring may optionally contain as one of the said ring atoms an oxygen or a sulfur atom, S(O), S(O)₂, or NR⁵;

R⁵ represents hydrogen, $C_{1-4}$alkyl, hydroxy$C_{1-4}$alkyl or $C_{1-4}$alkoxy$C_{1-4}$alkyl;

R⁶ represents hydrogen, $C_{1-6}$alkyl, fluoro$C_{1-6}$alkyl, $C_{3-7}$cycloalkyl, unsubstituted phenyl, or phenyl substituted with one or two groups selected from halogen, $C_{1-6}$alkyl, halo$C_{1-6}$alkyl, $C_{3-7}$cycloalkyl, $C_{1-6}$alkoxy or halo$C_{1-6}$alkoxy;

m is either zero or an integer from 1 to 4;

n is either zero or an integer from 1 to 3;

or a pharmaceutically acceptable salt, N-oxide or a prodrug thereof.

2. A compound according to claim 1 in which R¹ is halogen, $C_{1-4}$alkyl or fluoro$C_{1-4}$alkyl.

3. A compound according to claim 1 or 2 in which n is one or two.

4. A compound according to claim 1 in which R² is hydrogen, halogen, $C_{1-4}$alkyl, $C_{1-4}$alkoxy or phenyl substituted by $C_{1-4}$alkyl or fluoro$C_{1-4}$alkyl.

5. A compound according to claim 4 in which =W—X=Y— represents
=N—CH=CH—, =N—N=CH—, =N—CH=N— or =N—N=C(Ar₂)—.

6. A compound according to claim 1 in which Ar₁ represents a heterobicyclic ring system selected from isoquinoline, indazole, triazolopyridine, cinnoline, benzothiazole, imidazopyridine, quinoline, tetrahydroisoquinoline or dihydroisoquinoline.

7. A compound according to claim 1 in which Ar₂ is phenyl or pyridyl which are optionally fused to a phenyl, imidazolyl or thienyl ring, and are unsubstituted or substituted by one to three groups independently selected from halogen, cyano, $C_{1-4}$alkyl, fluoro$C_{1-4}$alkyl, $C_{1-4}$alkoxy, fluoro$C_{1-4}$alkoxy, phenyl$C_{1-2}$alkoxy, piperidine optionally substituted by oxygen, COR⁶ where R⁶ is hydrogen or $C_{1-4}$alkyl, pyrazole, $C_{1-4}$alkylcarbonyl, carboxy, $C_{1-6}$alkylsulphonyl, nitro, phenyl, $C_{1-4}$alkylthio, hydroxy and —O—CH₂—O—.

8. A pharmaceutical composition comprising a compound of formula (I) according to claim 1, or a pharmaceutically acceptable salt or N-oxide thereof, and a pharmaceutically acceptable excipient.

9. A compound of formula (I) according claim 1, or a pharmaceutically acceptable salt or N-oxide thereof, for use in a method of treatment of the human or animal body by therapy.

10. A method for the treating pain, which method comprises administration to a patient in need thereof of an effective amount of a compound of formula (I) according to claim 1, or a pharmaceutically acceptable salt or N-oxide thereof.

* * * * *